United States Patent
Benjamin et al.

(10) Patent No.: US 10,350,228 B2
(45) Date of Patent: Jul. 16, 2019

(54) TREATMENT OF SICKLE CELL DISEASE AND INFLAMMATORY CONDITIONS

(71) Applicants: Seattle Genetics, Inc., Bothell, WA (US); Regents of the University of Minnesota, Minneapolis, MN (US)

(72) Inventors: Dennis R. Benjamin, Bothell, WA (US); Nicole Okeley, Bothell, WA (US); Gregory Vercellotti, Minneapolis, MN (US); John D. Belcher, Minneapolis, MN (US)

(73) Assignees: Seattle Genetics, Inc., Bothell, WA (US); Regents of the University of Minnesota, Minneapolis, MN (US)

( * ) Notice: Subject to any disclaimer, the term of this patent is extended or adjusted under 35 U.S.C. 154(b) by 4 days.

(21) Appl. No.: 14/422,976

(22) PCT Filed: Aug. 22, 2013

(86) PCT No.: PCT/US2013/056223
§ 371 (c)(1),
(2) Date: Feb. 20, 2015

(87) PCT Pub. No.: WO2014/031875
PCT Pub. Date: Feb. 27, 2014

(65) Prior Publication Data
US 2015/0238509 A1    Aug. 27, 2015

Related U.S. Application Data

(60) Provisional application No. 61/692,567, filed on Aug. 23, 2012, provisional application No. 61/842,671, filed on Jul. 3, 2013.

(51) Int. Cl.
*A61K 31/7004* (2006.01)
*A61K 31/7024* (2006.01)
*A61K 31/7048* (2006.01)

(52) U.S. Cl.
CPC ...... *A61K 31/7004* (2013.01); *A61K 31/7024* (2013.01); *A61K 31/7048* (2013.01)

(58) Field of Classification Search
CPC ............ A61K 31/7004; A61K 31/7024; A61K 31/7048
USPC ......................................................... 514/23
See application file for complete search history.

(56) References Cited

U.S. PATENT DOCUMENTS

| | | |
|---|---|---|
| 4,407,817 A | 10/1983 | Chan |
| 5,034,517 A | 7/1991 | Umezawa et al. |
| 5,210,078 A | 5/1993 | Toyokuni et al. |
| 5,374,746 A | 12/1994 | Ok et al. |
| 5,461,143 A | 10/1995 | Wong et al. |
| 5,595,976 A | 1/1997 | Billington et al. |
| 5,770,407 A | 6/1998 | Wong et al. |
| 5,945,404 A | 8/1999 | Sugai et al. |
| 6,075,134 A | 6/2000 | Bertozzi et al. |
| 6,143,724 A | 11/2000 | Ohira et al. |
| 6,458,937 B1 | 10/2002 | Bertozzi et al. |
| 6,489,302 B1 | 12/2002 | Wiessler et al. |
| 6,713,287 B1 | 3/2004 | Wong |
| 6,936,701 B2 | 8/2005 | Bertozzi et al. |
| 6,979,675 B2 | 12/2005 | Tidmarsh |
| 7,160,865 B2 | 1/2007 | Lampidis et al. |
| 7,214,660 B2 | 5/2007 | DeFrees et al. |
| 7,265,084 B2 | 9/2007 | DeFrees et al. |
| 7,335,500 B2 | 2/2008 | Wong et al. |
| 7,351,408 B2 | 4/2008 | Bertozzi et al. |
| 7,968,687 B2 | 6/2011 | McDonagh et al. |
| 8,163,551 B2 | 4/2012 | Alley et al. |
| 8,242,167 B2 | 8/2012 | Lampidis et al. |
| 8,278,349 B2 | 10/2012 | Kloog et al. |
| 8,299,033 B2 | 10/2012 | Priebe et al. |
| 8,574,907 B2 | 11/2013 | Alley et al. |
| 8,633,021 B2 | 1/2014 | Xia et al. |
| 8,993,326 B2 | 3/2015 | Alley et al. |
| 9,504,702 B2 | 11/2016 | Senter et al. |
| 9,816,069 B2 | 11/2017 | Alley et al. |
| 2004/0132140 A1 | 7/2004 | Satoh et al. |
| 2005/0043250 A1 | 2/2005 | Lampidis et al. |
| 2006/0009400 A1 | 1/2006 | Eckhaerdt et al. |
| 2006/0246456 A1 | 11/2006 | Tsuchiya et al. |
| 2007/0190597 A1 | 8/2007 | Agnew et al. |
| 2007/0249014 A1 | 10/2007 | Agnew et al. |
| 2008/0026943 A1 | 1/2008 | Fischer et al. |
| 2008/0166756 A1 | 7/2008 | Tsuchiya et al. |
| 2009/0305972 A1 | 12/2009 | Chahal et al. |
| 2011/0003338 A1 | 1/2011 | Bayer et al. |
| 2011/0003758 A1 | 1/2011 | Priebe et al. |
| 2011/0097308 A1 | 4/2011 | Xia et al. |

(Continued)

FOREIGN PATENT DOCUMENTS

| | | |
|---|---|---|
| EP | 1 676 910 A1 | 7/2006 |
| JP | 2-504153 A | 11/1990 |

(Continued)

OTHER PUBLICATIONS

Xia et al. (Blood, Nov. 15, 2004, vol. 104, No. 10, pp. 3091-3096).*
Lard et al. (Journal of Leukocyte Biology vol. 66, Sep. 1999, 411-415).*
Araki et al. (Biochemical and Biophysical Research Communications 224, 825-830 (1996)).*
Nature Rev Drug Discov. Dec. 1, 2011;10(12):890.*
International Search Report corresponding to PCT/US2013/056223 dated Jan. 31, 2014, 3 pages.
International Search Report dated Nov. 25, 2009, for International Application No. PCT/US09/42610 filed on May 1, 2009, 4 pages.
Supplementary European Search Report, dated Oct. 11, 2012, corresponding to EP application No. 09 73 9983.6; 7 pages.
Supplementary European Search Report dated Dec. 19, 2015, corresponding to EP Application No. 13 83 1167; 11 pages.

(Continued)

*Primary Examiner* — Shaojia A Jiang
(74) *Attorney, Agent, or Firm* — Mintz Levin Cohn Ferris Glovsky and Popeo PC

(57) ABSTRACT

The invention provides methods and compositions for the treatment of sickle cell disease and other inflammatory conditions.

18 Claims, 8 Drawing Sheets

(56) References Cited

U.S. PATENT DOCUMENTS

Figure 4A:
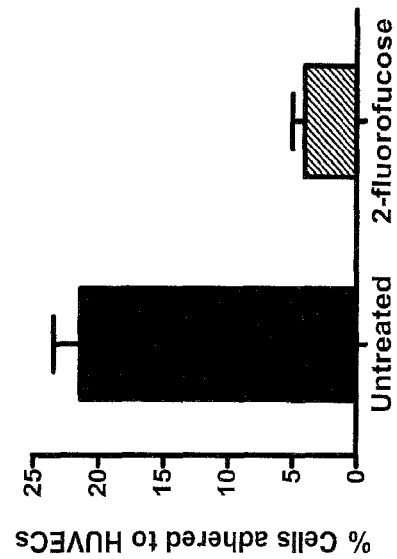

| | | | |
|---|---|---|---|
| 2012/0183997 | A1 | 7/2012 | Alley et al. |
| 2012/0202762 | A1 | 8/2012 | Magnani |
| 2012/0276108 | A1 | 11/2012 | Priebe |
| 2013/0129784 | A1* | 5/2013 | Senter ............... A61K 31/7004 424/277.1 |
| 2018/0155677 | A1 | 6/2018 | Alley et al. |

FOREIGN PATENT DOCUMENTS

| | | |
|---|---|---|
| JP | 6-507169 A | 8/1994 |
| WO | 89/10929 A2 | 11/1989 |
| WO | 92/19632 A1 | 11/1992 |
| WO | 98/25940 A1 | 6/1998 |
| WO | 98/054365 A1 | 12/1998 |
| WO | 2004/033651 A2 | 4/2004 |
| WO | 2004/091499 A2 | 10/2004 |
| WO | 2004/099231 A2 | 11/2004 |
| WO | 2007/048122 A2 | 4/2007 |
| WO | 2007/081031 A1 | 7/2007 |
| WO | 2007/111952 A2 | 10/2007 |
| WO | 2008/052030 A2 | 5/2008 |
| WO | 2009/108926 A1 | 9/2009 |
| WO | 2009/135181 A2 | 11/2009 |
| WO | 2009/143078 A2 | 11/2009 |
| WO | 2010/005735 A2 | 1/2010 |
| WO | 2010/111713 A2 | 9/2010 |
| WO | 2011/137527 A1 | 11/2011 |
| WO | 2012/019165 A2 | 2/2012 |
| WO | 2005/061523 A1 | 7/2015 |

OTHER PUBLICATIONS

Opposition filed Oct. 20, 2014 against EP U.S. Pat. No. 2282773 (corresponds to U.S. Pat. No. 8,163,551).

Invalidation Trial filed Jun. 5, 2015 against JP Patent No. 5624535 (corresponds to U.S. Pat. No. 8,163,551).

Albermann, Chrisotph et al. "Preparative Synthesis of GDP-β-L-Fucose by Recombinant Enzymes From Enterobacterial Sources," *Glycobiology* (Mar. 17, 2000); 10(9):875-881.

Alton, Gordon et al. "Direct Utilization of Mannose for Mammalian Glycoprotein Biosynthesis," *Glycobiology*, 1998, vol. 8, No. 3, pp. 285-295.

Aybay, Cemalettin et al., "Development of a rapid, single-step procedure using protein G affinity chromatography to deplete fetal calf serum of its IgG and to isolate murine IgG1 monoclonal antibodies from supernatants of hybridoma cells," *Journal of Immunological Methods* (2000; accepted Sep 27, 1999); 233:77-81.

Baisch, Gabi et al. "Synthetic Potential of Cloned Fucosyl-Transferase III and VI," *Bioorganic & Medicinal Chemistry Letters* (1997; accepted Aug. 18, 1997); 7(19):2447-2450.

Barbin, Karin et al., "Influence of Variable N-Glycosylation on the Cytolytic Potential of Chimeric CD19 Antibodies," *J. Immunother.* (Mar./Apr. 2006); 29(2):122-133.

Baskin, Jeremy et al. "Bioorthogonal Click Chemistry: Covalent Labeling in Living Systems," *QSAR Comb. Sci.* (Aug. 15, 2007); 26(11-12):1211-1219.

Beacham, Annabel et al. "Inhibition of Fucosyl Transferase and Fucosidase by a Rigid Bicyclic Mimic of α-L-Fucose," *Tetrahedron Letters* (1998; accepted Oct. 24, 2007); 39:151-154.

Becker, Daniel J. et al. "Fucose: Biosynthesis and Biological Function in Mammals," *Glycobiology* (Feb. 10, 2003); 13(7):41R-53R.

Braun, Curtis et al. "Mechanism-Based Inhibition of Yeast α-Glucosidase and Human Pancreatic α-Amylase by a New Class of Inhibitors," *The Journal of Biological Chemistry* (Nov. 10, 1995); 270(45):26778-26781.

Brown, Jillian R. et al. "Glycan Antagonists and Inhibitors: A Fount for Drug Discovery," *Critical Reviews in Biochemistry and Molecular Biology* (2007; published online Oct. 11, 2008); 42:481-515.

Burkart, Michael D. et al. "Chemo-Enzymatic Synthesis of Fluorinated Sugar Nucleotide: Useful Mechanistic Probes for Glycosyltransferases," *Bioorganic & Medicinal Chemistry* (Apr. 14, 2000); 8:1937-1946.

Butters, T. D. et al. "Molecular Requirements of Imino Sugars for the Selective Control of N-Linked Glycosylation and Glycosphingolipid Biosynthesis," *Tetrahedron: Asymmetry* (2000; accepted Oct. 25, 1999); 11:113-124.

Cai, Shaopei et al. "Synthesis of Carbocyclic Analogs of Guanosine 5'-(.Beta.-I-Fucopyranosyl Diphosphate) (GDP-Fucose) as Potential Inhibitors of Fucosyltransferases," *J. Org. Chem.* (Sep. 21, 1992); 57:6693-6696.

Calderón, Félix et al. "Structure/Activity Relationship of Carba- and C-Fucopyranosides as Inhibitors of an α1,6-Fucosyltransferase by Molecular Modeling and Kinetic Studies," *Letters in Organic Chemistry* (2005; accepted Nov. 11, 2004); 2:247-251.

Clark, Julia L. et al. "Expression of Human α-L-Fucosyltransferase Gene Homologs in Monkey Kidney COS Cells and Modification of Potential Fucosyltransferase Acceptor Substrates by an Endogenous Glycosidase," *Glycobiology* (1999; accepted Jul. 7, 1998); 9(2):191-202.

Codelli, Julian A. et al. "Second-Generation Difluorinated Cyclooctynes for Copper-Free Click Chemistry," *J. Am. Chem. Soc.*, (May 1, 2008); 130:11486-11493.

Compain, Philippe et al. "Carbohydrate Mimetics-Based Glycosyltransferase Inhibitors," *Bioorganic & Medicinal Chemistry* (Mar. 26, 2001); 9:3077-3092.

Compain, Philippe et al. "Design, Synthesis and Biological Evaluation of Iminosugar-Based Glycosyltransferase Inhibitors," *Current Topics in Medicinal Chemistry* (2003); 3:541-560.

Cummings, Varki A. et al, "Chapter 40 Natural and Synthetic Inhibitors of Glycosylation," *Essentials of Glcyobiology* (Cold Spring Harbor Laboratory Press; ©1999); 18 pages.

Derossi, Charles et al. "Ablation of Mouse Phosphomannose Isomerase (*Mpi*) Causes Mannose 6-Phosphate Accumulation, Toxicity, and Embryonic Lethality," *The Journal of Biological Chemistry* (2006; in Press Dec. 8, 2005); 281(9):5916-5927.

Ferrara, Claudia et al. "The Carbohydrate at FcγRIIIa Asn-162—An Element Required for High Affinity Binding to Non-Fucosylated IgG Glycoforms," *The Journal of Biological Chemistry* (2006; in Press Dec. 5, 2005); 281(8):5032-5036.

Fessner, Wolf-Dieter et al. "Enzymes in Organic Synthesis, 15 Short Enzymatic Synthesis of L-Fucose Analogs," *Eur. J. Org. Chem.* (2000); 15:125-132.

Fukuda, Minoru, *Cell Surface Carbohydrates and Cell Development*; (© 1992 by CRC Press, Inc.); Book cover; publication page; pp. 1-2.

Galan, M. Carmen et al. "The design and Synthesis of a Selective Inhibitor of Fucosyltransferase VI," *Org. Biomol. Chem.* (Apr. 1, 2004); 2:1376-1380.

Gamblin, David P. et al. "Glycoprotein Synthesis: An Update," *Chem. Rev.* (Apr. 20, 2009); 109:131-163.

Geng, Fei et al., "The expression of core fucosylated E-cadherin in cancer cells and lung cancer patients: prognostic implications," *Cell Research* (Jun. 18, 2004); 14(5):423-433.

González, Concepció C. et al., "Fragmentation of carbohydrate anomeric alkoxy radicals: A mew synthesis of chiral 1-halo-1-iodo Alditols," Chemistry—A European Journal, (Jan. 1, 2003); 9(23):5800-5809.

Goodarzi, M. T. et al., "Decreased branching, increased fucosylation and changed sialylation of alpha-1-proteinase inhibitor in breast and ovarian cancer," *Clinica Chimica Acta* (Feb. 13, 1995); 236:161-171.

Goon, Scarlett et al. "Metabolic Substrate Engineering as a Tool for Glycobiology," *Journal of Carbohydrate Chemistry* (Dec. 31, 2002); 21(7):943-977.

Gosselin, Sylvie et al. "A Continuous Spectrophotometric Assay for Glycosyltransferases," *Analytical Biochemistry* (1994); 220:92-97.

Gross, Volker et al. "Inhibition of Protein N-Glycosylation by 2-Deoxy-2-Fluoro-D-Galactose," *Biochem. J.* (Feb. 12, 1992); 285:821-826.

Grün, Bernhard R. et al. "Metabolism and Actions of 2-Deoxy-2-Fluoro-D-Galactose In Vivo," *Eur. J. Biochem.* (1990); 190:11-19.

(56) References Cited

OTHER PUBLICATIONS

Haltiwanger, Robert S., "Fucose Is on the Trail of Colon Cancer," *Gastroenterology* (May 1, 2009) 137(1):36-39.

Hanson, Sarah R. et al. "Probing Glycans With the Copper(I)-Catalyzed [3+2] Azide—Alkyne Cycloaddition," *QSAR Comb. Sci.* (Sep. 27, 2007); 26(11-12):1243-1252.

Hsu, Tsui-Ling et al. "Alkynyl sugar analogs for the labeling and visualization of glycoconjugates in cells," *PNAS*, (Feb. 20, 2007); 104(8):2614-2619.

Ichikawa, Yoshitaka et al. "Chemical-Enzymatic Synthesis and Conformational Analysis of Sialyl Lewis x and Derivatives," *J. Am. Chem. Soc.* (Jun. 4, 1992); 114:9283-9298.

Ihara, Hideyuki et al. "Reaction Mechanism and Substrate Specificity for Nucleotide Sugar of Mammalian α1,6-Fucosyltransferase—A Large-Scale Preparation and Characterization of Recombinant Human FUT8," *Glycobiology* (2006; Advance Access Pub Dec. 11, 2005); 16(4): 333-342.

Ihara, Hideyuki et al. "Crystal Structure of Mammalian α1,6-fucosyltransferase, FUT8," *Glycobiology* (2007; Advance Access Pub Dec. 15, 2006); 17(5):455-466.

Iida, Shigeru et al. "Nonfucosylated Therapeutic IgG1 Antibody Can Evade the Inhibitory Effect of Serum Immunoglobulin G on Antibody-Dependent Cellular Cytotoxicity Through Its High Binding to FcγRIIIa," *Clin Cancer Res.* (May 1, 2006); 12(9):2879-2887.

Imahori, Y. et al "2-Deoxy-2-[$^{18}$F]Fluoro-L-Fucose, A Potential Agent for Regional Fucose Utilization Studies Associated with Glycoprotein Synthesis," *CYRIC Annual Report* (1984); 12 pages.

Imai-Nishiya, Harue et al. "Double knockdown of α1,6-fucosyltransferase (*FUT8*) and GDP-mannose 4,6-dehydratase (*GMD*) in antibody-producing cells: a new strategy for generating fully non-fucosylated therapeutic antibodies with enhanced ADCC," *BMC Biotechnology* (Nov. 30, 2007); 7:84; 13 pages.

Ishiwata, Kiichi, et al. "6-[$^{18}$F] Fluoro-L-fucose: A Possible Tracer for Assessing Glycoconjugate Synthesis in Tumors with Positron Emission Tomography," *J. Nucl. Med.* (May 10, 1990); 31:1997-2003.

Jefferis, Roy "Glycosylation as a Strategy to Improve Antibody-Based Therapeutics," *Nature Reviews Drug Discovery* (Mar. 2009); 8:227-234.

Jones, Mark B. et al. "Characterization of the Cellular Uptake and Metabolic Conversion of Acetylated N-Acetylmannosamine (ManNAc) Analogues to Sialic Acids," *Biotechnology and Bioengineering* (Feb. 20, 2004); 85(4):394-405.

Kamińska, J. et al., "Chemical modifications of α1,6-fucosyltransferase define amino acid residues of catalytic importance," *Biochimie* (Jan. 28, 2003); 85:303-310.

Kanda, Yutaka et al. "Comparison of Biological Activity Among Nonfucosylated Therapeutic IgG1 Antibodies with Three Different N-Linked Fc Oligosaccharides: The High-Mannose, Hybrid, and Complex Types," *Glycobiology* (Sep. 25, 2006); 17(1):104-118.

Kanda, Yutaka et al. "Establishment of a GDP-Mannose 4,6-Dehydratase (*GMD*) Knockout Host Cell Line: A New Strategy for Generating Completely Non-Fucosylated Recombinant Therapeutics," *Journal of Biotechnology* (Apr. 23, 2007); 130:300-310.

Kim, Eun Jeong et al. "Characterization of the Metabolic Flux and Apoptotic Effects of O-Hydroxyl-and N-Acyl-modified N-Acetylmannosamine Analogs in Jurkat Cells," *The Journal of Biological Chemistry*, (Feb. 13, 2004); 279(18):18342-18352.

Kötzler, Miriam P. et al., "Donor Assists Acceptor Binding and Catalysis of Human α1,6- Fucosyltransferase," *ACS Chemical Biology* (Jun. 3, 2013); 8:1830-1840.

Laughlin, Scott T. et al. "Metabolic Labeling of Glycans with Azido Sugars and Subsequent Glycan-Profiling and Visualization via Staudinger Ligation," *Nature Protocols* (Nov. 15, 2007); 2(11):2930-2944.

Laughlin, Scott T. et al. "Imaging the Glycome," *PNAS* (Jan. 6, 2009); 106(1):12-17.

Lee, Ho H. et al. "Analogs of Cell Surface Carbohydrates. Synthesis of D-Galactose Derivatives Having an Ethynyl, Vinyl or Epoxy Residue at C-5," *Carbohydrate Research* (1988; accepted for pub revised form May 15, 1987); 176:59-72.

Lee Lac V. et al. "A Potent and Highly Selective Inhibitor of Human α-1,3-Fucosyltransferase via Click Chemistry," *J. Am. Chem. Soc.* (May 7, 2003); 125:9588-9589.

Lim, Amareth et al. "Glycosylation Profiling of a Therapeutic Recombinant Monoclonal Antibody with Two N-Linked Glycosylation Sites Using Liquid Chromatography Coupled to a Hybrid Quadrupole Time-of-Flight Mass Spectrometer," *Analytical Biochemistry* (Jan. 9, 2008); 375:163-172.

Luchansky, Sarah J. et al. "Expanding the Diversity of Unnatural Cell-Surface Sialic Acids," *ChemBioChem* (2004); 5:371-374.

Lühn, Kerstin et al. "The gene defective in leukocyte adhesion deficiency II encodes a putative GDP-fucose transporter," *Nature Genetics* (May 2001; accepted Mar. 28, 2001); 28:69-72.

Maeda, Takahiro et al. "FRET-Based Direct and Continuous Monitoring of Human Fucosyltransferases Activity: An Efficient synthesis of Versatile GDP-L-Fucose Derivatives from Abundant D-Galactose," *Chem. Eur. J.* (2008; published online Oct. 11, 2007); 14:478-487.

Matsumura, Kengo et al. "Carbohydrate Binding Specificity of a Fucose-specific Lectin From *Aspergillus oryzae*—A Novel Probe for Core Fucose," *The Journal of Biological Chemistry* (Feb. 8, 2007); 282(21):15700-15708.

May, Jr. Jesse A., et al. "Synthesis and Biological Activity of Potential Antimetabolites of L-Fucose," *Journal of Medicinal Chemistry*, 1979, vol. 22, No. 8, pp. 971-976.

Miyoshi, Eiji et al., "Fucosylated haptoglobin is a novel marker for pancreatic cancer: Detailed analysis of oligosaccharide structures," *Proteomics* (Mar. 28, 2008); 8:3257-3262.

Mori, Katsuhiro et al. "Engineering Chinese Hamster Ovary Cells to Maximize Effector Function of Produced Antibodies Using FUT8 siRNA," *Biotechnology and Bioengineering* (Aug. 26, 2004); 88(7):901-908.

Mori, Katsuhiro et al. "Non-Fucosylated Therapeutic Antibodies: The Next Generation of Therapeutic Antibodies," *Cytotechnology* (Oct. 31, 2007); 55:109-114.

Moriwaki, Kenta et al., "Fucosylation and gastrointestinal cancer," *World J. Hepatol.* (Apr. 27, 2010); 2(4):151-161.

Murray, Brion W. et al. "Mechanism of Human α-1,3-Fucosyltransferase V: Glycosidic Cleavage Occurs Prior to Nucleophilic Attack," *Biochemistry* (1997; revised manuscript); 36:823-831.

Niittymäki, Jaana "GDP-L-Fucose: Synthesis and Role in Inflammation," Academic Dissertation Mar. 23, 2007, Department of Bacteriology and Immunology, Haartman Institute and Biomedicum Helsinki and Division of Biochemistry, Department of Biological and Environmental Sciences, Faculty of Biosciences University of Helsinki and Glycoscience Graduate School; pp. 7-54.

Norris, Andrew et al. "Inhibition Kinetics of Carba- and C-fucosyl Analogues of GDP-Fucose Against Fucosyltransferase v: Implication for the Reaction Mechanism," *Bioorganic & Medicinal Chemistry Letters* (2004; accepted Dec. 2, 2003); 14:571-573.

Okeley, Nicole et al., "Enhancement of antibody effector function activities through biochemical inhibition of fucosylation," Abstract No. 608 (2011); 1 page.

Okeley, Nicole M. et al., "Development of orally active inhibitors of protein and cellular fucosylation," *PNAS* (Apr. 2, 2013); 110(14):5404-5409.

Omasa Takeshi et al. "Decrease in Antithrombin III Fucosylation by Expressing GDP-Fucose Transporter siRNA in Chinese Hamster Ovary Cells," *Journal of Bioscience and Bioengineering* (May 15, 2008); 106(2):168-173.

Ortmann, Monika et al., "Sialylated glycoconjugates in chromophobe cell renal carcinoma compared with other renal cell tumors," *Virchows Archiv B Cell Pathol* (Jun. 6, 1991); 61:123-132.

Pan, Y. T. et al. "Castanospermine Inhibits the Processing of the Oligosaccharide Portion of the Influenza Viral Hemagglutinin," *Biochemistry* (Aug. 2, 1983); 22:3975-3984.

Panneerselvam, K. et al. "Human Fibroblasts Prefer Mannose over Glucose as a Source of Mannose for N-Glycosylation," *The Journal of Biological Chemistry* (Jun. 10, 1997); 272(37):23123-23129.

Papac, Damon I. et al. "A High-Throughput Microscale Method to Release N-Linked Oligosaccharides From Glycoproteins for Matrix-

(56) References Cited

OTHER PUBLICATIONS

Assisted Laser Desorption/Ionization Time-of-Flight Mass Spectrometric Analysis," *Glycobiology* (1998; accepted Dec. 15, 1997); 8(5):445-454.

Park, Dongkyu et al. "Characterization and Role of Fucose Mutarotase in Mammalian Cells," *Glycobiology* (Jun. 15, 2007); 17(9):955-962.

Park, Sungjin et al. "Chemical Tools for Functional Studies of Glycans," *Chem. Soc. Rev.* (Mar. 11, 2008); 37:1579-1591.

Peipp, Matthias et al. "Antibody Fucosylation Differentially Impacts Cytotoxicity Mediated by NK and PMN Effector Cells," *Blood* (Pre-published online Jun. 19, 2008; doi:10.1182/blood-2008-03-144600); 29 pages.

Prescher, Jennifer A. et al., "Chemistry in Living Systems," *Nature Chemical Biology* (Jun. 1, 2005); 1(1):13-21.

Qiao, Lei et al. "Synergistic Inhibition of Human α-1,3-Fucosyltransferase V," *J. Am. Chem. Soc.* (Jan. 25, 1996); 118:7653-7662.

Rabuka, David et al. "A Chemical Reporter Strategy to Probe Glycoprotein Fucosylation," *J. Am. Chem. Soc.* (Jun. 29, 2006); 28:12078-12079.

Rillahan, Cory D. et al., "Global Metabolic Inhibitors of Sialyl-and Fucosyltransferases Remodel the Glycome," *Nature Chemical Biology* (Jul. 2012; published online Jun. 10, 2012 DOI:10.1038/NCHEMBIO.999); 8:661-668.

Rillahan, Cory D., "High-Throughput Screening for Inhibitors of Sialyl- and Fucosyltransferases," *Angew. Chem. Int. Ed.* (Nov. 9, 2011); 59:12534-12537.

Sampathkumar, Srinivasa-Gopalan et al. "Metabolic Installation of Thiols into Sialic Acid Modulates Adhesion and Stem Cell Biology," *Nature Chemical Biology* (Mar. 2006; published online Feb. 12, 2006); 2(3):149-152.

Sawa, Masaaki et al. "Glycoproteomic Probes for Fluorescent Imaging of Fucosylated Glycans In Vivo," *PNAS* (Aug. 15, 2006); 103(33):12371-12376.

Saxon, Eliana et al. "Investigating Cellular Metabolism of Synthetic Azidosugars with the Staudinger Ligation," *J. Am. Chem. Soc.* (Jul. 17, 2002); 124:14893-14902.

Schuster, Manfred et al. "Improved Effector Functions of a Therapeutic Monoclonal Lewis Y-Specific Antibody by Glycoform Engineering," *Cancer Res.* (Sep. 1, 2005); 65(17):7934-7941.

Schwartz, Reinhard et al., "Glycoconjugates of Murine Tumor Lines with Different Metastatic Capacities. I. Differences in Fucose Utilization and in Glycoprotein Patterns," *Int. J. Cancer* (Feb. 2, 1984); 33:503-509.

Sheid, B. et al. "Enzymatic formation of potential anticancer and antiviral inosine analogues," *Experientia* (Jun. 11, 1996);52:878-881.

Shinkawa, Toyohide et al., "The absence of fucose but not the presence of galactose or bisecting N-acetylglucosamine of human IgG1 complex-type oligosaccharides shows the critical role of enhancing antibody-dependent cellular cytotoxicity," *Journal of Biological Chemistry*, (Jan. 31, 2003); 278(5):3466-3473.

Sommers, Linda Wyles et al., "Transport of Sugar Nucleotides into Rat Liver Golgi," *The Journal of Biological Chemistry* (Sep. 25, 1982; rec'd for publication Mar. 25, 1982); 257(18):10811-10817.

Speers, Anna E. et al., "Proteomics of Integral Membrane Proteins—Theory and Application," *Chem. Rev.* (published on Web Aug. 8, 2007); 107:3687-3714.

Staü ňková, Jana et al., "Fucose-Activated Killer (FAK) Cells: Anomalous Killers With Augmented Cytotoxic Activity," *The Journal of Immunology* (Dec. 6, 1985); 135(6):3718-3728.

Sturla Laura et al. "Expression, Purification and Characterization of GDP-D-Mannose 4,6-Dehydratase From *Escherichia coli*," *FEBS Letters* (Jun. 4, 1997); 412:126-130.

Sufrin, Janice R. et al. "Halogenated L-Fucose and D-Galactose Analogs: Synthesis and Metabolic Effects," *J. Med. Chem.* (1980); 23(2):143-149.

Takahashi Tomoaki et al. "A Sequence Motif Involved in the Donor Substrate Binding by α1,6-fucosyltransferase: the Role of the Conserved Residues," *Glycobiology* (2000; accepted Nov. 15, 1999); 10(5):503-510.

Tanaka Toru et al. "Design and Synthesis of Peptide Mimetics of GDP-Fucose: Targeting Inhibitors of Fucosyltransferases," *Synlett* (2004); 2:243-246.

Tarling Chris A. et al. "Identification of the Catalytic Nucleophile of the Family 29 α-L-Fucosidase from *Thermotoga maritima* through Trapping of a Covalent Glycosyl-Enzyme Intermediate and Mutagenesis," *The Journal of Biological Chemistry* (Sep. 15, 2003); 278(48): 47394-47399.

Ulgar Victor et al. "New N-Alkylsulfonamides and Alkyl Sulfonates Derived From 6-C-Sulfosugars," *Tetrahedron* (Jul. 15, 2002); 58:7967-7973.

Vagin, Olga et al., "Inverse Correlation between the Extent of N-Glycan Branching and Intercellular Adhesion in Epithelia," *The Journal of Biological Chemistry* (Jan. 25, 2008); 283(4):2192-2202.

Valero-González, Jessika et al., "A proactive role of water molecules in acceptor recognition by Protein O-fucosyltransferase 2," *Nature Chemical Biology* (Apr. 201; published online Feb. 8, 2016 DOI:101038/NCHEMBIO.2019); 12:240-246.

Vocadlo David J. et al. "A Chemical Approach for Identifying O-GlcNAc-Modified Proteins in Cells," *PNAS* (Aug. 5, 2003); 100(16):9116-9121.

Vogel Chr. et al. "Galacturonate aus Acetyl- und Isopropyliden-D-Galactopyranosen," *Journal f. prakt. Chemie. Band* (1990); 332(1):28-36, translation of Abstract only.

Vogel C. et al. "Synthesis of C-Glycosidic Galacturopates Suitable as Glycosyl Acceptors," *Polish J. Chem.* (2005); 79:251-265.

Von Ahsen Oliver et al. "A Miniaturized High-Throughput Screening Assay for Fucosyltransferase VII," *Analytical Biochemistry* (2008; avail online Aug. 28, 2007); 372:96-105.

Walsh, Gary et al., "Post-translational modifications in the context of therapeutic proteins," *Nature Biotechnology* (Oct. 10, 2006); 24(10):1241-1252.

Wang, Qianli et al. "Efficient Glycoengineering of GM3 on Melanoma Cell and Monoclonal Antibody-Mediated Selective Killing of the Glycoengineered Cancer Cell," *Bioorganic & Medicinal Chemistry* (Sep. 12, 2007); 15:7561-7567.

Wang, Xiangchun et al., "Core Fucosylation Regulates Epidermal Growth Factor Receptor-mediated intracellular Signaling," *Journal of Biological Chemistry* (Feb. 3, 2006); 281(5):2572-2577.

Ward, Peter et al, "Monoclonal Antibody Production," *Committee on Methods of Producing Monoclonal Antibodies, Institute for Laboratory Animal Research, National Research Council* (© 1999 National Academy of Sciences); ISBN: 0-309-51904-7, 75 pages.

Watt, Gregory et al. "Site-Specific Glycosylation of an Aglycosylated Human IgG1-Fc Antibody Protein Generates Neoglycoproteins with Enhanced Function," *Chemistry & Biology* (Sep. 19, 2003); 10:807-814.

Wilkinson Brendan L., et al. "Click Chemistry in Carbohydrate Based Drug Development and Glycobiology," In: *Drug Design Research Perspectives*; Chapter IV; Editor: Stanley P. Kaplan, Nova Science Publishers, Inc. © 2007, pp. 57-102.

Winterbourne, D. J. et al. "2-Deoxy-2-Fluoro-L-Fucose and Its Effect on L-[1-$^{14}$C] Fucose Utilization in Mammalian Cells," *Biochemical and Biophysical Research Communications* (Feb. 23, 1979); 87:989-992.

Wright, Ann et al. "Effect of Altered $C_H2$-associated Carbohydrate Structure on the Functional Properties and In Vivo Fate of Chimeric Mouse-Human Immunoglobulin G1," *J. Exp. Med.*, (Sep. 1, 1994); 180:1087-1096.

Wright, Ann et al. "In Vivo Trafficking and Catabolism of IgG1 Antibodies with Fc Associated Carbohydrates of Differing Structure," *Glycobiology* (Aug. 16, 2000); 10(12):1347-1355.

Wrodnigg, Tanja M. et al. "Natural and Synthetic Iminosugars as Carbohydrate Processing Enzyme Inhibitors for Cancer Therapy," *Anti-Cancer Agents in Medicinal Chemistry* (2008; accepted Nov. 13, 2006); 8:77-85.

Wuts, Peter G. M., "Reactivities, Reagents, and Reactivity Charts," *Green's Protective Groups in Organic Synthesis* (published online Aug. 11, 2014; DOI:10.1002/9781118905074.ch10); pp. 406-416.

(56) References Cited

OTHER PUBLICATIONS

Yamaguchi, Yoshiki et al. "Glycoform-Dependent Conformational Alteration of the Fc Region of Human Immunoglobulin G1 as Revealed by NMR Spectroscopy," *Biochimica et Biophysica Acta* (2006; avail online Oct. 26, 2005); 1760:693-700.

Yuan, Kun et al., "Cell Surface Associated Alpha-L-Fucose Moieties Modulate Human Breast Cancer Neoplastic Progression," *Pathol. Oncol. Res.* (Jun. 13, 2008); 14:145-156.

Yurchenco, Peter D. et al. "Fucosyl-Glycoprotein and Precursor Pools in HeLa Cells," *Biochemistry* (1975); 14(14):3107-3114.

Yurchenco, Peter D. et al. "Equilibration of Fucosyl Glycoprotein Pools in HeLa Cells," *Biochemistry* (1977); 16(5):944-953.

Zeitler, R. et a., Inhibition of L-Fucokinase from Ra Liver by L-Fucose Analogies In Vitro (1997); 11:265-273.

Zeng, Ying et al. "High-Efficiency Labeling of Sialylated Glycoproteins on Living Cells," *Nature Methods* (Mar. 2009; published online Feb. 22, 2009); 6(3):207-209.

Zhao, Yangyang et al. "Deletion of Core Fucosylation on $\alpha 3\beta 1$ Integrin Down-Regulates Its Functions," *The Journal of Biological Chemistry* (Oct. 16, 2006); 281(50):38343-38350.

Zhou, Qun et al. "Development of a Simple and Rapid Method for Producing Non-Fucosylated Oligomannose Containing Antibodies With Increased Effector Function," *Biotechnology and Bioengineering* (2008; published online Aug. 6, 2007); 99(3):652-665.

Zips, Daniel et al., "New Anticancer Agents: In Vitro and In Vivo Evaluation," In Vivo (2005; accepted Nov. 25, 2004); 19:1-8.

Zola, Heddy *Monoclonal Antibodies: A Manual of Techniques*; (© 1987 by CRC Press, Inc.); Book cover; title and publication pages; pp. 26-27.

Chang, Jungshan et al., "GMI-1070, a novel pan-selectin antagonist, reverses acute vascular occlusions in sickle cell mice," *Blood* (Sep. 9, 2010) 116(10):1779-1786.

\* cited by examiner

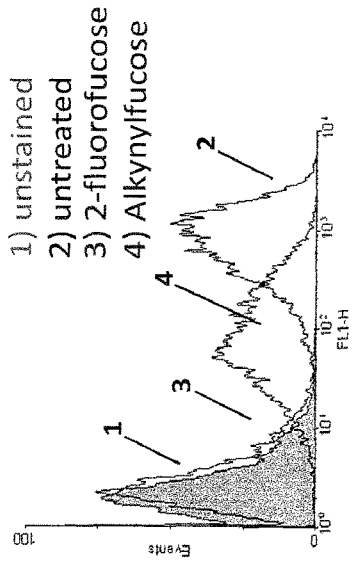
Fig. 1A
LCA: generic fucose
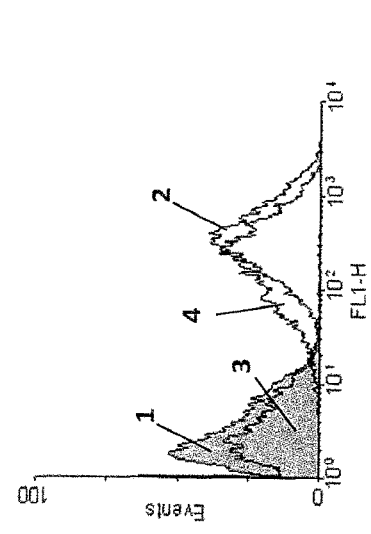
Fig. 1B
UEA-1: (1→2)-linked
Fig. 1C
Anti-SSEA-1: Lewis<sup>x</sup> (1→3)
1) unstained
2) untreated
3) 2-fluorofucose
4) Alkynylfucose
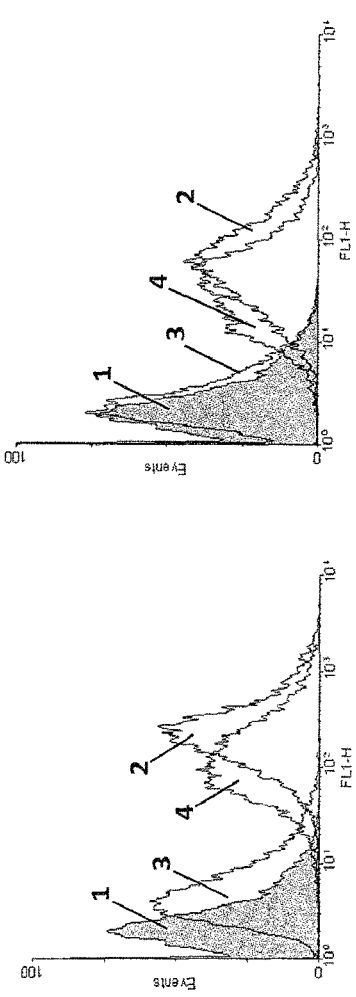
Fig. 1D
AAL: (1→2),(1→3),(1→6)
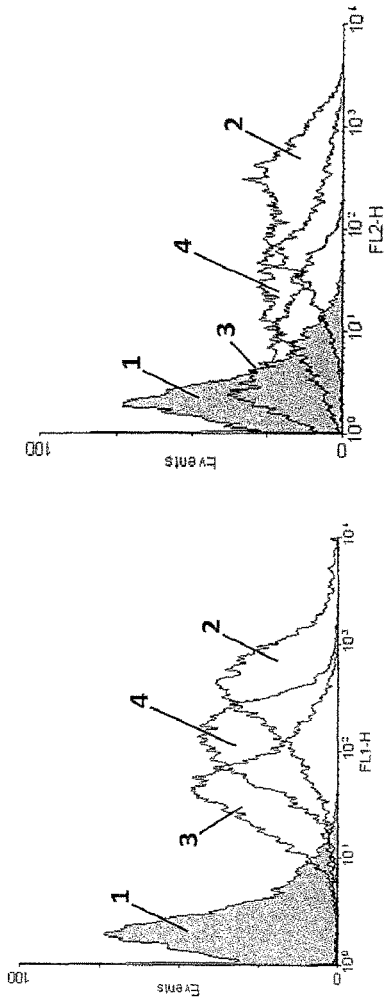
Fig. 1E
Anti-Sialyl Le<sup>x</sup>: (1→3)
Fig. 1F
Anti-Lewis Y: (1→3), (1→2)

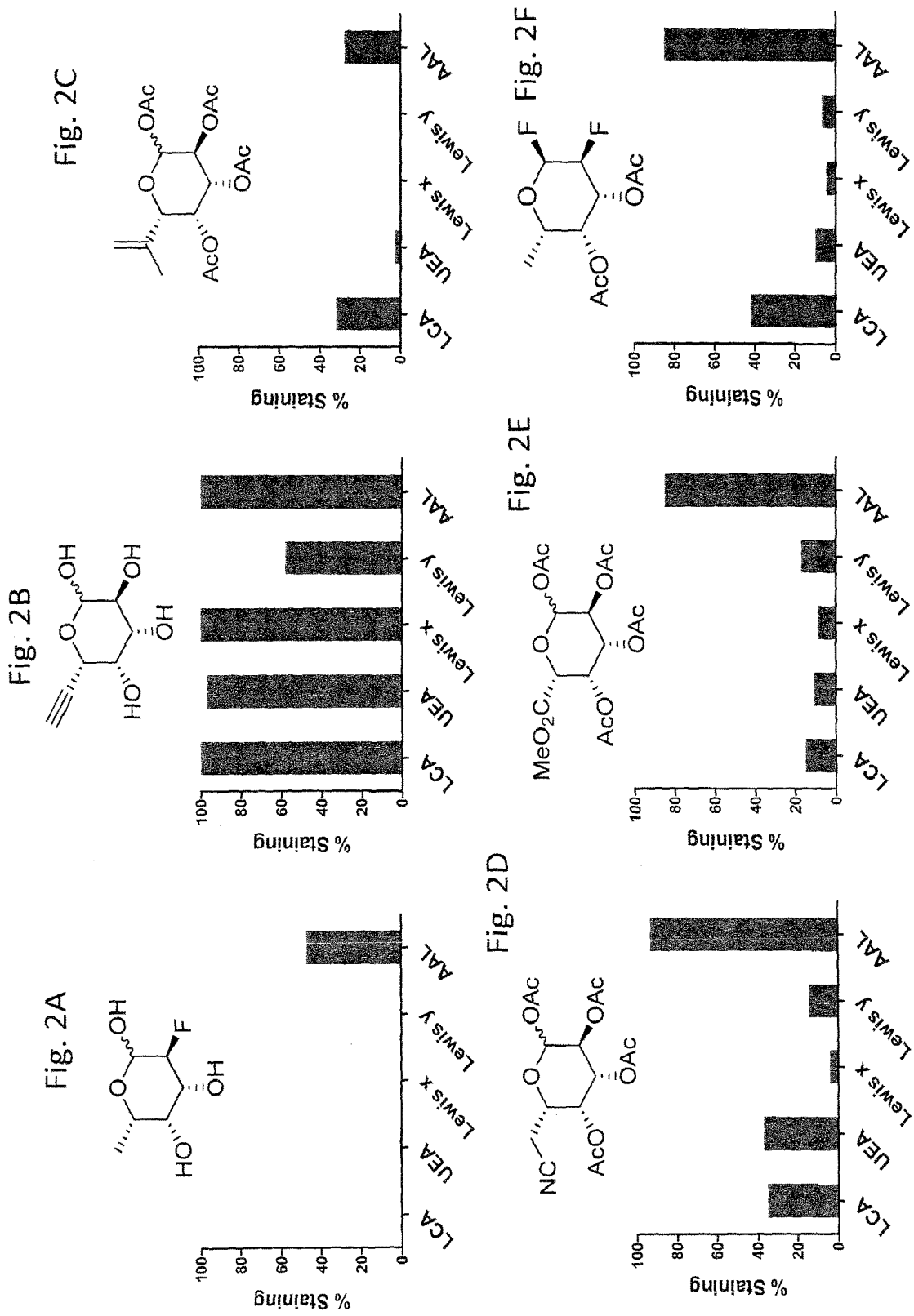

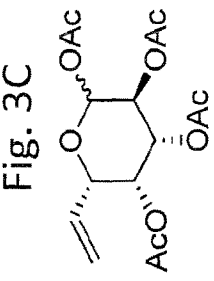
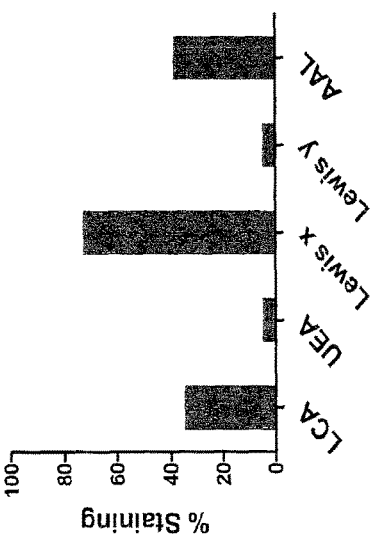
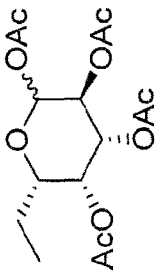
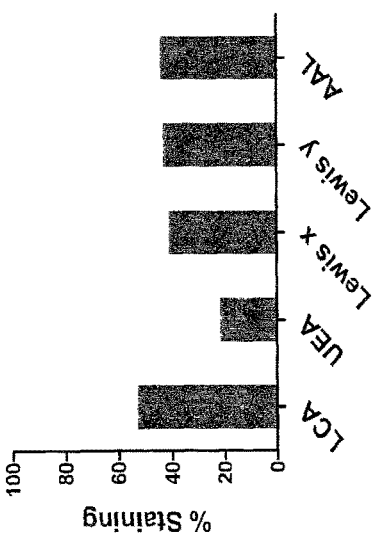
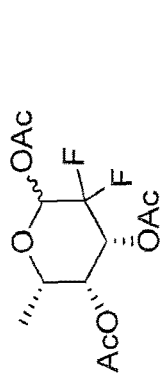
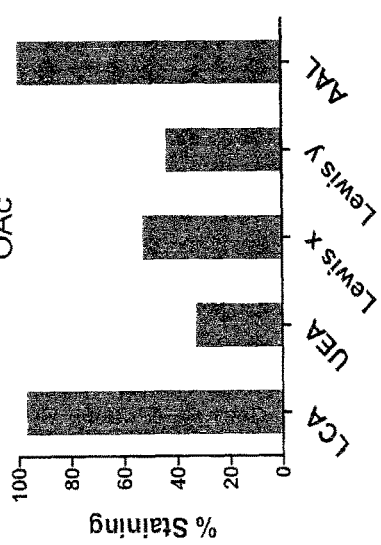
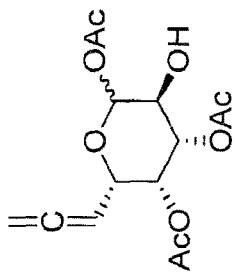
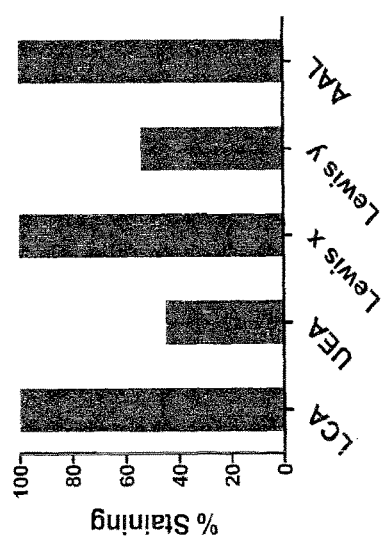

TREATMENT OF SICKLE CELL DISEASE AND INFLAMMATORY CONDITIONS

This application claims the benefit of U.S. Provisional Patent Application No. 61/692,567, filed Aug. 23, 2012, and U.S. Provisional Patent Application No. 61/842,671, filed Jul. 3, 2013, each of which is incorporated herein in its entirety and for all purposes.

BACKGROUND

Sickle cell disease is a genetic blood disorder characterized by red blood cells that assume an abnormal rigid sickle shape and is caused by a genetic mutation in the B-globin chain of the hemoglobin gene. Sickle cell disease can result in anemia and other clinical crisis including vaso-occlusive crisis and multiple organ damage. Adhesive interactions between circulating sickle red blood cells, leukocytes and endothelial cells have been implicated in the development of vaso-occlusion and evidence indicates that sickle cell disease is a state of inflammation characterized by vascular endothelial activation and increased blood cell-endothelium interactions. Contributors to the increased adhesion of sickle red blood cells to the endothelium and the development of vaso-occlusive crisis include cell adhesion molecules such as P-selectin and E-selectin. Methods of interrupting the adhesion interactions between sickle red blood cells, leukocytes and the endothelium are needed. This invention addresses this and other needs.

SUMMARY

In one aspect, methods and compositions for the treatment of sickle cell disease are provided. In some aspects, such treatment reduces the incidence of vaso-occlusion in a subject having sickle cell disease or reduces the severity or duration of a vaso-occlusive event in a subject having sickle cell disease.

In another aspect, methods and compositions for the treatment of vascular obstruction or vaso-occlusion are provided, including methods for reducing the incidence of vaso-occlusion or reducing the severity or duration of a vaso-occlusive event in a subject. In some aspects, the vaso-occlusion is associated with sickle cell disease. In another aspect, methods and compositions for the inhibition of inflammation are provided, e.g., vascular inflammation. In some aspects, the inflammation is associated with sickle cell disease. The methods include the step of administering a fucose analog (as provided herein) to an animal in need thereof. In some aspects, the fucose analog is 2-fluorofucose or a fucose analog that, when administered to a subject, is converted in vivo to 2-fluorofucose.

In some aspects, administration of a fucose analog (as provided herein) inhibits the binding of adhesion molecules (e.g., E-selectin, P-selectin) to cells (e.g., white blood cells e.g., neutrophils) in an animal. In some aspects, administration of a fucose analog (as provided herein) inhibits leukocyte capture of red blood cells, including sickle red blood cells, in an animal. In some aspects, administration of a fucose analog (as provided herein) inhibits leukocyte rolling along on the endothelium in an animal. In some aspects, administration of a fucose analog (as provided herein) inhibits leukocyte adhesion (e.g., neutrophil adhesion) to the endothelium in an animal. In some aspects, administration of a fucose analog (as provided herein) inhibits neutrophil extravasation in an animal.

These and other aspects of the present invention may be more fully understood by reference to the following detailed description, non-limiting examples of specific embodiments, and the appended figures.

DRAWINGS

FIGS. 1A-1F show FACS analysis of the effects of 2-fluorofucose or alkynyl fucose on cell surface fucosylation. The staining reagents employed bind to fucose-containing epitopes on the cell surface. A decrease in staining demonstrates a decrease in the binding of these fucose-dependent reagents to the cell surfaces.

FIGS. 2A-2F show FACS analysis of the effects of select fucose analogs on cell surface fucosylation. The staining reagents employed bind to fucose-containing epitopes on the cell surface. A decrease in staining demonstrates a decrease in the binding of these fucose-dependent reagents to the cell surfaces.

FIGS. 3A-3D show FACS analysis of the effects of select fucose analogs on cell surface fucosylation. The staining reagents employed bind to fucose-containing epitopes on the cell surface. A decrease in staining demonstrates a decrease in the binding of these fucose-dependent reagents to the cell surfaces.

Figure 4B:
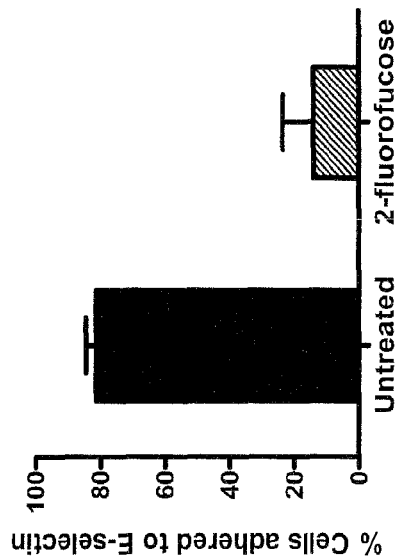

FIGS. 4A-4B demonstrate the effects of 2-fluorofucose on cell adhesion to E-selectin or activated HUVEC cells. Interaction of LS174T tumor cells with immobilized E-selectin or HUVEC cells activated with TNFα was measured at 4° C. and demonstrates decreased adhesion of cells after treatment with 2-fluorofucose.

Figure 5B:
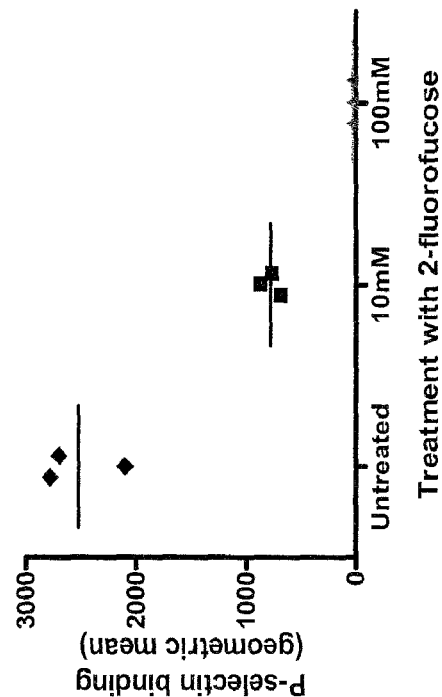
Figure 5A:
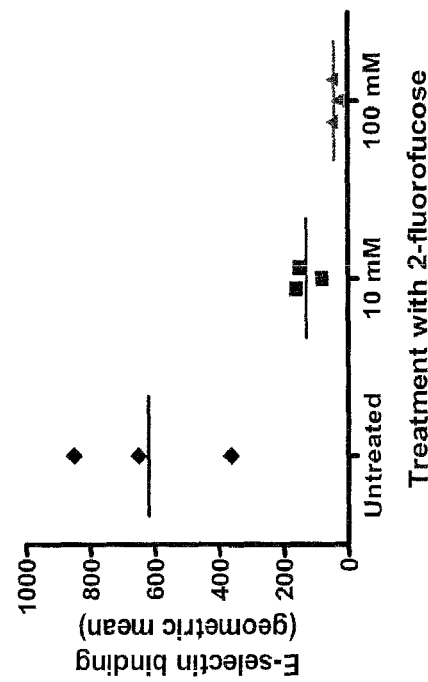

FIGS. 5A-5B shows the effect of 2-fluorofucose on inhibition of E-selectin or P-selectin binding to neutrophils isolated from mice treated with increasing concentrations of 2-fluorofucose. The functional binding of P-selectin to neutrophils is dimished with increasing 2-fluorofucose treatment.

Figure 6:
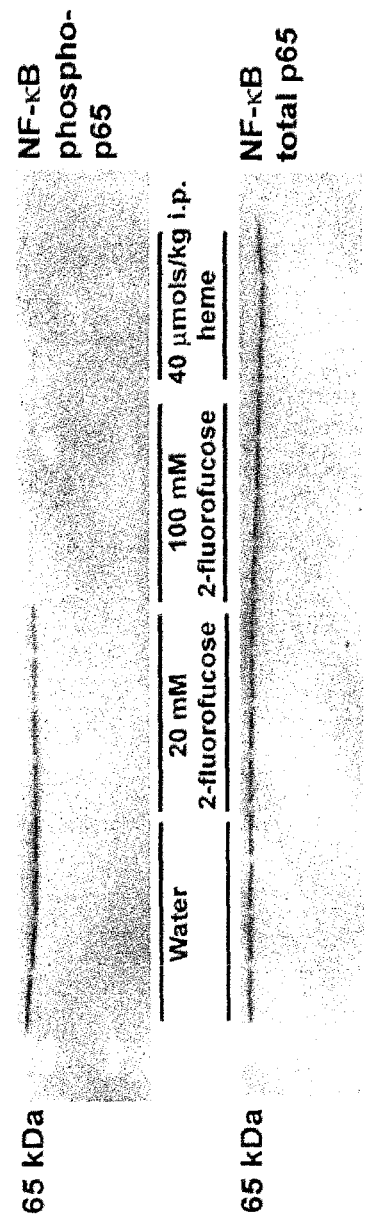
Figure 7:
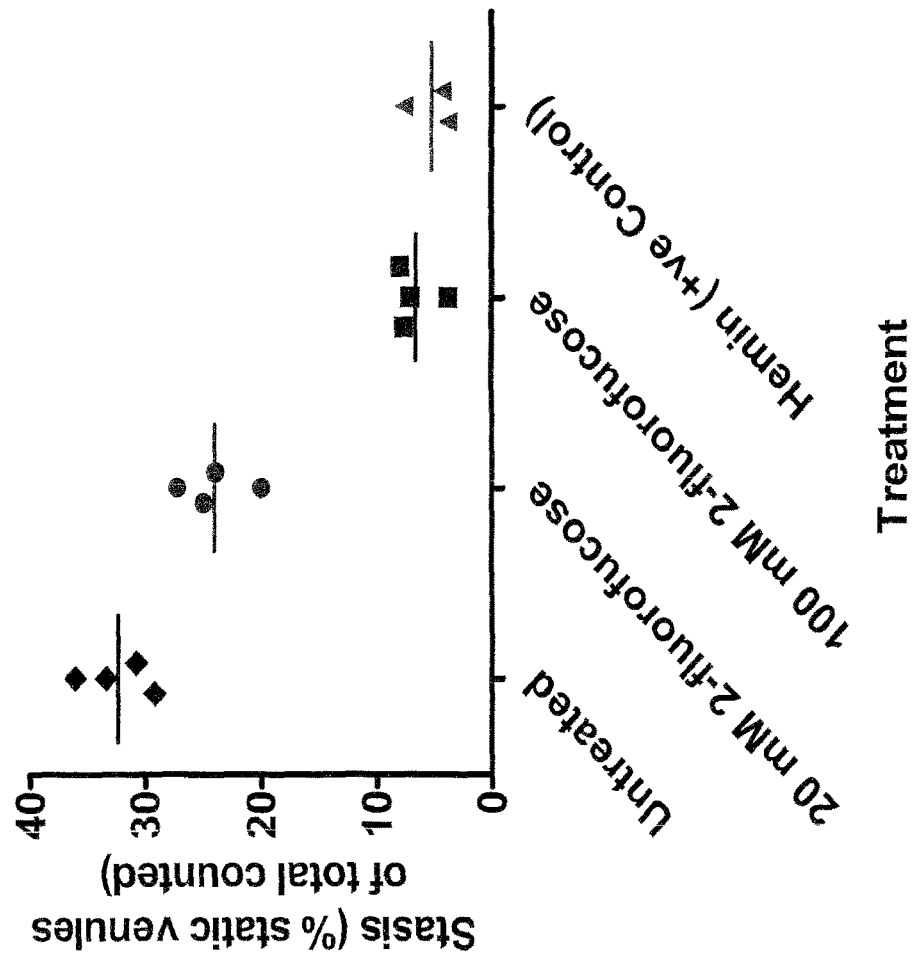

FIG. 6 shows a western blot of NF-κB phospho p65 in liver nuclear extracts of 2-fluorofucose treated sickle cell mice. Nuclear NF-κB phospho-p65 was partially diminished in mice treated with 20 mM 2-fluorofucose and markedly decreased in mice treated with 100 mM 2-fluorofucose or heme FIG. 7 shows the percent static venules in control sickle mice and sickle mice pretreated with 2-fluorofucose, measured 1 hour following induction of vascular statis. Vascular stasis was partially diminished in mice treated with 20 mM 2-fluorofucose and markedly decreased in mice treated with 100 mM 2-fluorofucose or heme.

Figure 8:
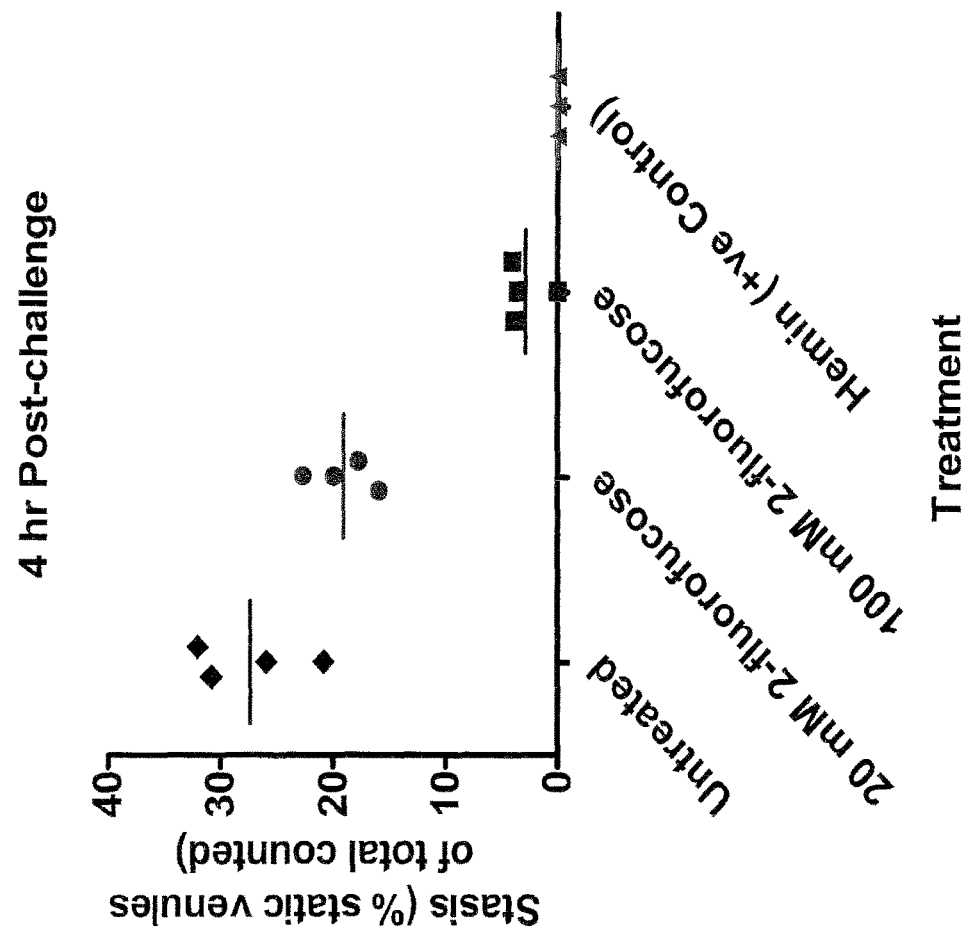

FIG. 8 shows the percent static venules in control mice and mice pretreated with 2-fluorofucose, measured 4 hours following induction of vascular statis. Vascular stasis was partially diminished in mice treated with 20 mM 2-fluorofucose and markedly decreased in mice treated with 100 mM 2-fluorofucose or heme.

DETAILED DESCRIPTION

Definitions

The terms "inhibit" or "inhibition of" means to reduce by a measurable amount, or to prevent entirely. The term inhibition as used herein can refer to an inhibition or reduction of at least about 10%, at least about 15%, at least about 20%, at least about 25%, at least about 30%, at least about 35%, at least about 40%, at least about 50%, at least about 60%, at least about 70%, at least about 80%, at least about 90%, at least about 95%, or at least about 99%.

The terms "treatment" or "treat" refer to slowing, stopping, or reversing the progression of the disease or condition in a patient, as evidenced by a decrease or elimination of a clinical or diagnostic symptom of the disease or condition. Treatment can include, for example, a decrease in the severity of a symptom, the number of symptoms, or frequency of relapse. Treatment can include reduction of endothelial injury in a subject. In some aspects, treatment of sickle cell disease refers to preventing or reducing vascular obstruction associated with sickle cell disease, reducing the incidence of vaso-occlusion in a subject having sickle cell disease, and/or reducing the severity or duration of a vaso-occlusive event in a subject having sickle cell disease. Preventing or reducing vascular obstruction associated with sickle cell disease, reducing the incidence of vaso-occlusion in a subject having sickle cell disease, and/or reducing the severity or duration of a vaso-occlusive event in a subject having sickle cell disease can have the effect of reducing or preventing pain associated with sickle cell disease (e.g., sickle cell crisis) and preventing or reducing the severity of life threatening conditions associated with repeated vaso-occlusive events (e.g., stroke, acute chest syndrome, pulmonary hypertension, organ failure). Treatment can result in a decrease in the use of pain medication/narcotics by patients and shortened hospital stays.

The term "effective amount," in the context of the administration of a fucose analog refers to the amount of the analog that is sufficient to have the desired effect, e.g., treatment of sickle cell disease.

As used herein, "hydrolyzable ester or ether groups" refers to any conventional ester or ether, which can be hydrolyzed in vivo to yield the hydroxy group. Exemplary hydrolyzable ester and ether groups include —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), —OC(O)$C_2$-$C_{10}$ alkynylene(heterocycle), —OC(O)$CH_2O$($CH_2CH_2O$)$_n$$CH_3$, —OC(O)$CH_2CH_2O$($CH_2CH_2O$)$_n$$CH_3$, —O-tri-$C_1$-$C_3$ alkyl silyl, —OC$_1$-$C_{10}$ alkyl, —OCH$_2$OC(O) alkyl, —OCH$_2$OC(O) aryl, —OCH$_2$OC(O)O alkyl, and —OCH$_2$OC(O)O aryl, wherein each n is an integer independently selected from 0-5.

As used herein, the term "vaso-occlusion" refers to the occlusion or restriction in lumen diameter of a blood vessel. In some embodiments, vaso-occlusion is associated with or caused by an inflammatory response. In some embodiments, vaso-occlusion is associated with sickle cell disease. In some aspects, vaso-occlusion or vaso-occlusive crisis associated with sickle cell is caused by sickle-shaped red blood cells that obstruct capillaries and restrict blood flow to an organ, resulting in ischaemia, pain, necrosis, and often, organ damage.

As used herein, "alkynyl fucose peracetate" refers to any or all forms of alkynyl fucose (5-ethynylarabinose) with acetate groups on positions $R^{1-4}$ (see formula I and II, infra), including 6-ethynyl-tetrahydro-2H-pyran-2,3,4,5-tetrayl tetraacetate, including the (2S,3S,4R,5R,6S) and (2R,3S,4R,5R,6S) isomers, and 5-((S)-1-hydroxyprop-2-ynyl)-tetrahydrofuran-2,3,4-triyl tetraacetate, including the (2S,3S,4R,5R) and (2R,3S,4R,5R) isomers, and the aldose form, unless otherwise indicated by context. The terms "alkynyl fucose triacetate", "alkynyl fucose diacetate" and "alkynyl fucose monoacetate" refer to the indicated tri-, di- and mono-acetate forms of alkynyl fucose, respectively.

Unless otherwise indicated by context, the term "alkyl" refers to an unsubstituted saturated straight or branched hydrocarbon having from 1 to 20 carbon atoms (and all combinations and subcombinations of ranges and specific numbers of carbon atoms therein), unless otherwise specified. An alkyl group of 1 to 3, 1 to 8 or 1 to 10 carbon atoms is preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, when substituted can be substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), aryl, —C(O)R', —OC(O)R', —C(O)OR', —C(O)$NH_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from —H, —$C_1$-$C_8$ alkyl, —$C_2$-$C_8$ alkenyl, —$C_2$-$C_8$ alkynyl, or aryl.

Unless otherwise indicated by context, the terms "alkenyl" and "alkynyl" refer to unsubstituted or optionally substituted (were indicated) straight and branched carbon chains having from 2 to 20 carbon atoms (and all combinations and subcombinations of ranges and specific numbers of carbon atoms therein), with from 2 to 3, 2 to 4, 2 to 8 or 2 to 10 carbon atoms being preferred. An alkenyl chain has at least one double bond in the chain and an alkynyl chain has at least one triple bond in the chain. Examples of alkenyl groups include, but are not limited to, ethylene or vinyl, allyl, -1 butenyl, -2 butenyl, -isobutylenyl, -1 pentenyl, -2 pentenyl, 3-methyl-1-butenyl, -2 methyl 2 butenyl, and -2,3 dimethyl 2 butenyl. Examples of alkynyl groups include, but are not limited to, acetylenic, propargyl, acetylenyl, propynyl, -1 butynyl, -2 butynyl, -1 pentynyl, -2 pentynyl, and -3 methyl 1 butynyl.

Alkenyl and alkynyl groups, whether alone or as part of another group, when substituted can be substituted with one or more groups, preferably 1 to 3 groups (and any additional substituents selected from halogen), including but not limited to: halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from H, —$C_1$-$C_8$ alkyl, —$C_2$-C alkenyl, —$C_2$-$C_8$ alkynyl, or aryl.

Unless otherwise indicated by context, the term "alkylene" refers to an unsubstituted saturated branched or straight chain hydrocarbon radical having from 1 to 20 carbon atoms (and all combinations and subcombinations of ranges and specific numbers of carbon atoms therein), with from 1 to 8 or 1 to 10 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like.

Alkylene groups, whether alone or as part of another group, when substituted can be substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or -aryl.

"Alkenylene" refers to an unsaturated, branched or straight chain or cyclic hydrocarbon radical of an alkenyl group (as described above), and having two monovalent radical centers derived by the removal of two hydrogen atoms from the same or two different carbon atoms of a parent alkene. An "alkenylene" group can be unsubstituted or optionally substituted (were indicated), as described above for alkenyl groups. In some embodiments, an "alkenylene" group is not substituted.

"Alkynylene" refers to an unsaturated, branched or straight chain or cyclic hydrocarbon radical of an alkynyl group (as described above), and having two monovalent radical centers derived by the removal of two hydrogen atoms from the same or two different carbon atoms of a parent alkyne. An "alkynylene" group can be unsubstituted or optionally substituted (were indicated), as described above for alkynyl groups. In some embodiments, an "alkynylene" group is not substituted.

Unless otherwise indicated by context, the term "aryl" refers to a substituted or unsubstituted monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to: halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, —$NO_2$, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or aryl.

Unless otherwise indicated by context, the term "heterocycle" refers to a substituted or unsubstituted monocyclic ring system having from 3 to 7, or 3 to 10, ring atoms (also referred to as ring members) wherein at least one ring atom is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocyclic heterocycle preferably has 3 to 7 ring members (e.g., 2 to 6 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960). Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, fucosyl, azirdinyl, azetidinyl, oxiranyl, oxetanyl, and tetrahydrofuranyl.

A heterocycle group, whether alone or as part of another group, when substituted can be substituted with one or more groups, preferably 1 to 2 groups, including but not limited to: —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or -aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; or position 2, 3, or 4 of an azetidine. Exemplary carbon bonded heterocycles can include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; and position 4 of a morpholine. Still more typically, nitrogen bonded heterocycles include 1-aziridyl, 1-azetidyl, 1-pyrrolyl, 1-imidazolyl, 1-pyrazolyl, and 1-piperidinyl.

Unless otherwise noted, the term "carbocycle," refers to a substituted or unsubstituted, saturated or unsaturated non-aromatic monocyclic ring system having from 3 to 6 ring atoms (and all combinations and subcombinations of ranges and specific numbers of carbon atoms therein) wherein all of the ring atoms are carbon atoms.

Carbocycle groups, whether alone or as part of another group, when substituted can be substituted with, for example, one or more groups, preferably 1 or 2 groups (and any additional substituents selected from halogen), including, but not limited to: halogen, $C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or aryl.

Examples of monocyclic carbocylic substituents include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, cyclooctyl, -1,3-cyclohexadienyl, -1,4-cyclohexadienyl, -1,3-cycloheptadienyl, -1,3,5-cycloheptatrienyl, and -cyclooctadienyl.

When any variable occurs more than one time in any constituent or in any formula, its definition in each occurrence is independent of its definition at every other. Combinations of substituents and/or variables are permissible only if such combinations result in stable compounds.

Unless otherwise indicated by context, a hyphen (-) designates the point of attachment to the pendant molecule. Accordingly, the term "—($C_1$-$C_{10}$ alkylene)aryl" or "—$C_1$-$C_{10}$ alkylene(aryl)" refers to a $C_1$-$C_{10}$ alkylene radical as defined herein wherein the alkylene radical is attached to the pendant molecule at any of the carbon atoms of the alkylene radical and one of the hydrogen atom bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are active and chemically stable and that can be readily synthesized by techniques known in the art as well as those methods set forth herein.

The term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which the fucose analog is administered.

"Small electron-withdrawing groups" refers to any substituent that has greater electronegativity at the site of substituent attachment than, e.g., a hydrogen atom or hydroxy group or relative to the substituent present in fucose at that site. Generally, the small electron-withdrawing group has 10 or fewer atoms (other than hydrogen) and includes groups such as nitro; cyano and cyanoalkyl (e.g., —$CH_2CH_2CN$); halogens; acetylene or other alkynes or halo alkynes (e.g., —C≡$CCF_3$); alkenes or halo alkenes; allenes; carboxylic acids, ester, amides and halo substituted forms thereof; sulfonic and phosphonic acids, esters and amides, and halo substituted forms thereof; haloalkyl groups (e.g., —$CF_3$, —$CHF_2$, —$CH_2CF_3$), acyl and haloacyl groups (e.g., —C(O)$CH_3$ and —C(O)$CF_3$); alkylsulfonyl and haloalkylsulfonyl (e.g., —S(O)$_2$alkyl and —S(O)$_2$haloalkyl); aryloxy (e.g., phenoxy and substituted phenoxy); aralkyloxy (e.g, benzyloxy and substituted benzyloxy); and oxiranes. Preferred small electron-withdrawing groups are those having 8, 7 or 6 or fewer atoms (other than hydrogen).

The fucose analogs are typically substantially pure from undesired contaminant. This means that the analog is typically at least about 50% w/w (weight/weight) purity, as well as being substantially free from interfering proteins and other contaminants. Sometimes the agents are at least about 80% w/w and, more preferably at least 90% or about 95% w/w purity. Using conventional purification techniques, homogeneous product of at least 99% w/w can be obtained.

General

The present invention, in based, in part, on the discovery that fucose analogs can act to inhibit vaso-occlusion in a mammal having disease, and, in particular, fucose analogs capable of inhibiting binding of adhesion molecules to neutrophils, can act to inhibit vaso-occlusion in a mammal having disease. Accordingly, provided herein, inter alia, are methods and compositions for the treatment of sickle disease, the treatment of vascular obstruction or vaso-occlusion, and/or the treatment of inflammation (e.g., vascular inflammation) in a mammal. In order to effect treatment, a fucose analog is administered to a subject in need thereof. Preferred fucose analogs to be used in the present invention are those that are capable of inhibiting binding of the adhesion molecules E-selectin and P-selectin to neutrophils. In some aspects, inhibition is a reduction of at least about 50%, at least about 60%, at least about 70%, at least about 80%, at least about 90%, at least about 95%, or at least about 99%.

In some aspects, the fucose analog will be administered in an amount that inhibits the formation of cell surface fucosylated carbohydrates in a subject thereby reducing cellular fucosylation. In some aspects, the fucose analog will be administered in an amount that inhibits the formation of fucoslyated proteins in a subject including fucosylated glycoproteins thereby reducing protein fucosylation. "Reduced fucosylation" generally refers to reduced addition of fucose to glycans via α(1,2)-, α(1,3)-, α(1,4)- and/or α(1,6)-linkages. In some aspects, the fucose analog inhibits the formation of fucosylated selectins in a subject. In other aspects, the fucose analog inhibits the formation of Lewis Y, Lewis X, Sialylated Lewis A and/or sialylated Lewis X, $SLe^X$, in a subject. By inhibiting the formation of cell surface carbohydrates, including, for example, Lewis X, sialyl Lewix X, sialyl Lewis A, and/or Lewis Y, adhesion events between leukocytes (e.g., neutrophils) and the endothelium can be reduced as well as interactions between sickle red blood cells and leukocytes. In some aspects, this reduction in adhesion events and reduced interactions between sickle red blood cells and leukocytes acts to prevent and/or reduce vascular obstruction (e.g., vaso-occlusive events) associated with sickle cell disease. In some aspects, reduction in adhesion events between leukocytes (e.g., neutrophils) and the endothelium acts to reduce inflammation in a subject suffering from inflammatory disease.

In the various aspects described herein, the subject to which the fucose analog is administered is typically a mammal and is preferably human. The invention therefore further provides methods and compositions for treating sickle disease, treating vascular obstruction or vaso-occlusion, and treating inflammation in a mammal, such as a human in need thereof. In some aspects, the human has sickle cell disease. In some aspects, the human has an acute or chronic inflammatory disease.

A subject to be treated with the methods of the present invention can be one that has been diagnosed with sickle cell disease. The subject can be identified as having sickle cell disease prior to administration of the fucose analog. As noted, sickle cell disease is characterized by red blood cells that assume an abnormal rigid sickle shape and is caused by a genetic mutation in the B-globin chain of the hemoglobin gene. Sickle cell disease encompasses a group of symptomatic disorders and is generally defined by the presence of hemoglobin S. The genotype of patients with sickle cell disease is typically HbSS, but other hemoglobin variants can cause symptomatic sickle cell disease, including HbSC, HbSD, HbSE, and sickle/beta thalassemia. Diagnosis can be by methods known in the art. Administration of the fucose analog to the subject having sickle cell disease can be at any time during the progression of the disease. For example, in some aspects, treatment with the fucose analog will be while the subject is experiencing a symptom of the disease, for example, severe pain. In other aspects, treatment with the fucose analog will be preventative in nature and will be administered to a subject having sickle cell disease prior to experiencing one or more symptoms of the disease. Such subjects may have experienced symptoms in the past but are being treated with the fucose analog in order to reduce the severity or incidence of future symptoms of the disease. Accordingly, in some aspects, the fucose analog will be administered to the subject while the subject is not experiencing noticeable symptoms of the disease, such as, for example, sickle cell crisis, whereas, in other aspects, the fucose analog will be administered to the subject while the subject is experiencing noticeable symptoms of the disease, such as, for example, sickle cell crisis.

In some aspects, the subjects to be treated with the methods of the present invention are those that have been diagnosed with inflammatory disease (e.g., vascular inflammatory disease). Diagnosis can be by methods known in the art. In some aspects, treatment will reduce the severity and/or duration of inflammation in the subject.

Fucose Analogs

Suitable fucose analogs for the methods provided herein include those that can be safely administered to a mammal in an amount effective to treat sickle cell disease, vascular obstruction or vaso-occlusion, and/or inflammation in a mammal, such as a human in need thereof.

In some embodiments, a fucose analog (or an intracellular metabolite or product of the fucose analog) inhibits an enzyme(s) in the fucose salvage pathway. (As used herein, an intracellular metabolite can be, for example, a GDP-modified analog or a fully or partially de-esterified analog. A product can be, for example, a fully or partially de-esterified analog.) For example, a fucose analog (or an intracellular metabolite or product of the fucose analog) can inhibit the activity of fucokinase, or GDP-fucose-pyrophosphorylase. In some embodiments, a fucose analog (or an intracellular metabolite or product of the fucose analog) inhibits fucosyltransferase (such as a 1,2-fucosyltransferase, 1,3-fucosyltransferase, 1,4-fucosyltransferase, or 1,6-fucosyltransferase (e.g., the FUT8 protein)). In some embodiments, a fucose analog (or an intracellular metabolite or product of the fucose analog) can inhibit the activity of an enzyme in the de novo synthetic pathway for fucose. For example, a fucose analog (or an intracellular metabolite or product of the fucose analog) can inhibit the activity of GDP-mannose 4,6-dehydratase or/or GDP-fucose synthetase. In some embodiments, the fucose analog (or an intracellular metabolite or product of the fucose analog) can inhibit a fucose transporter (e.g., GDP-fucose transporter).

In any of the various embodiments herein, the fucose analog can be any fucose analog that (i) inhibits the activity of GDP-mannose 4,6-dehydratase, and (ii) reduces the concentration of GDP-fucose. In some aspects, inhibition of the activity of GDP-mannose 4,6-dehydratase is by at least 50% and reduction of the concentration of GDP-fucose is by at least 50%. In some aspects, inhibition of the activity of GDP-mannose 4,6-dehydratase by at least 80% and reduction of the concentration of GDP-fucose is by at least 80%. Methods of determining whether a molecule can inhibit the activity of an enzyme such as GDP-mannose 4,6-dehydratase or reduce the concentration of GDP-fucose are known.

In any of the various embodiments herein, exemplary fucose analogs are those that can be shown to (i) inhibit the binding of adhesion molecules (e.g., E-selectin, P-selectin) to cells (e.g., white blood cells e.g., neutrophils) and/or (ii) inhibit cell adhesion interactions. In some aspects, inhibition is by at least at least 50%, at least 60%, at least 70%, at least 80%, or at least 90%. Methods of determining whether a fucose analog can inhibit the binding of adhesion molecules (e.g., E-selectin and/or P-selectin) to neutrophils and/or can inhibit cell adhesion interactions are provided in the examples section. See, examples 2 and 3.

In some aspects, administration of a fucose analog (as provided herein) inhibits leukocyte capture of red blood cells, including sickle red blood cells, in an animal. In some aspects, administration of a fucose analog (as provided herein) inhibits leukocyte rolling along on the endothelium in an animal. In some aspects, administration of a fucose analog (as provided herein) inhibits leukocyte adhesion (e.g., neutrophil adhesion) to the endothelium in an animal. In some aspects, administration of a fucose analog (as provided herein) inhibits neutrophil extravasation in an animal.

In any of the various embodiments herein, the fucose analog can have the following formula (I) or (II):

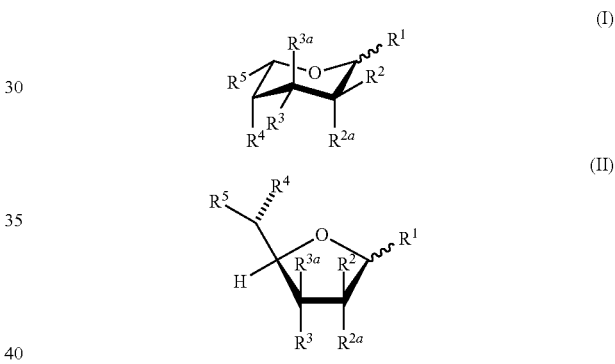

or a pharmaceutically acceptable salt or solvate form thereof, wherein each of formula (I) or (II) can be the alpha or beta anomer or the corresponding aldose form; and wherein, each of $R^1$, $R^2$, $R^{2a}$, $R^3$, $R^{3a}$ and $R^4$ is independently selected from the group consisting of —OH, a hydrolyzable ether group, a hydrolyzable ester group, and a small electron withdrawing group, wherein each n is an integer independently selected from 0-5; or each of $R^1$, $R^2$, $R^{2a}$, $R^3$, $R^{3a}$ and $R^4$ is independently selected from the group consisting of —OH, a hydrolyzable ether group, a hydrolyzable ester group, and a small electron withdrawing group, wherein each n is an integer independently selected from 0-5

$R^5$ is a member selected from the group consisting of —$CH_3$, —$CHX_2$, —$CH_2X$, —CH(X)—$C_1$-$C_4$ alkyl unsubstituted or substituted with halogen, —CH(X')—$C_2$-$C_4$ alkene unsubstituted or substituted with halogen, —CH(X')—$C_2$-$C_4$ alkyne unsubstituted or substituted with halogen, —CH=C($R^{10}$)($R^{11}$), —C($CH_3$)=C($R^{12}$)($R^{13}$), —C($R^{14}$)=C=C($R^{15}$)($R^{16}$), —$C_3$ carbocycle unsubstituted or substituted with methyl or halogen, —CH(X')—$C_3$ carbocycle unsubstituted or substituted with methyl or halogen, $C_3$ heterocycle unsubstituted or substituted with methyl or halogen, —CH(X')—$C_3$ heterocycle unsubstituted or substituted with methyl or halogen, —$CH_2N_3$, —$CH_2CH_2N_3$, and benzyloxymethyl, or $R^5$ is a small electron withdrawgroup; wherein $R^{10}$ is hydrogen or $C_1$-$C_3$ alkyl unsubstituted or substituted with halogen; $R^{11}$ is $C_1$-$C_3$ alkyl unsubstituted or substituted with halogen; $R^{12}$ is hydrogen, halogen or $C_1$-$C_3$ alkyl unsubstituted or substituted with halogen; $R^{13}$ is hydrogen, or $C_1$-$C_3$ alkyl unsubstituted or substituted with halogen; $R^{14}$ is hydrogen or methyl; $R^{15}$ and $R^{16}$ are independently selected from hydrogen, methyl and halogen; X is halogen; X' is halogen or hydrogen; and additionally, each of $R^1$, $R^2$, $R^{2a}$, $R^3$ and $R^{3a}$ are optionally hydrogen; optionally two $R^1$, $R^2$, $R^{2a}$, $R^3$ and $R^{3a}$ on adjacent carbon atoms are combined to form a double bond between said adjacent carbon atoms; and provided that at least one of $R^1$, $R^2$, $R^{2a}$, $R^3$, $R^{3a}$, $R^4$ and $R^5$ is a small electron withdrawing group, or $R^5$ comprises a halogen, site of unsaturation, carbocycle, heterocycle or azide.

The fucose analog can have formula (I) or (II), or a pharmaceutically acceptable salt or solvate form thereof, wherein each of $R^1$, $R^2$, $R^{2a}$, $R^3$, $R^{3a}$ and $R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), —OC(O)$C_2$-$C_{10}$ alkynylene(heterocycle), —OC(O)$CH_2O(CH_2CH_2O)_nCH_3$, —OC(O)$CH_2CH_2O(CH_2CH_2O)_nCH_3$, —O-tri-$C_1$-$C_3$ alkyl silyl, —O$C_1$-$C_{10}$ alkyl, —O$CH_2OC(O)$ alkyl, —O$CH_2OC(O)$ aryl, —O$CH_2OC(O)O$ alkyl, and —O$CH_2OC(O)O$ aryl and a small electron withdrawing group, wherein each n is an integer independently selected from 0-5;

$R^5$ is a member selected from the group consisting of —$CH_3$, —$CHX_2$, —$CH_2X$, —CH(X')—$C_1$-$C_4$ alkyl unsubstituted or substituted with halogen, —CH(X')—$C_2$-$C_4$ alkene unsubstituted or substituted with halogen, —CH(X')—$C_2$-$C_4$ alkyne unsubstituted or substituted with halogen, —CH=C($R^{10}$)($R^{11}$), —C($CH_3$)=C($R^{12}$)($R^{13}$), —C($R^{14}$)=C=C($R^{15}$)($R^{16}$), —$C_3$ carbocycle unsubstituted or substituted with methyl or halogen, —CH(X')—$C_3$ carbocycle unsubstituted or substituted with methyl or halogen, $C_3$ heterocycle unsubstituted or substituted with methyl or halogen, —CH(X')—$C_3$ heterocycle unsubstituted or substituted with methyl or halogen, —$CH_2N_3$, —$CH_2CH_2N_3$, and benzyloxymethyl, or $R^5$ is a small electron withdrawing group; wherein $R^{10}$ is hydrogen or $C_1$-$C_3$ alkyl unsubstituted or substituted with halogen; $R^{11}$ is $C_1$-$C_3$ alkyl unsubstituted or substituted with halogen; $R^{12}$ is hydrogen, halogen or $C_1$-$C_3$ alkyl unsubstituted or substituted with halogen; $R^{13}$ is hydrogen, or $C_1$-$C_3$ alkyl unsubstituted or substituted with halogen; $R^{14}$ is hydrogen or methyl; $R^{15}$ and $R^{16}$ are independently selected from hydrogen, methyl and halogen; X is halogen; X' is halogen or hydrogen; and additionally, each of $R^1$, $R^2$, $R^{2a}$, $R^3$ and $R^{3a}$ are optionally hydrogen; optionally two $R^1$, $R^2$, $R^{2a}$, $R^3$ and $R^{3a}$ on adjacent carbon atoms are combined to form a double bond between said adjacent carbon atoms; and provided that at least one of $R^1$, $R^2$, $R^{2a}$, $R^3$, $R^{3a}$, a $R^4$ and $R^5$ is a small electron withdrawing group, or $R^5$ comprises a halogen, site of unsaturation, carbocycle, heterocycle or azide.

The fucose analog can have formula (I) or (II), or a pharmaceutically acceptable salt or solvate form thereof, wherein each of $R^1$, $R^2$, $R^{2a}$, $R^3$, $R^{3a}$ and $R^4$ is independently selected from the group consisting of fluoro, chloro OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), —OC(O)$C_2$-$C_{10}$ alkynylene(heterocycle), —O$CH_2OC(O)$ alkyl, —O$CH_2OC(O)O$ alkyl, —O$CH_2OC(O)$ aryl, —O$CH_2OC(O)O$ aryl, —OC(O)$CH_2O(CH_2CH_2O)_nCH_3$, —OC(O)$CH_2CH_2O(CH_2CH_2O)_nCH_3$, —O-tri-$C_1$-$C_3$ alkylsilyl, and —O$C_1$-$C_{10}$ alkyl. $R^5$ is as defined herein.

The fucose analog can have formula (I) or (II), or a pharmaceutically acceptable salt or solvate form thereof, wherein each of $R^1$-$R^4$ is independently selected from the group consisting of fluoro, chloro, —OH, a hydrolyzable ester group, and a hydrolyzable ether group; each of $R^{2a}$ and $R^{3a}$ is independently selected from the group consisting of H, F, and Cl; and $R^5$ is selected from the group consisting of —$CH_3$, —CH=C=$CH_2$, —C≡CH, —C≡$CCH_3$, —$CH_2$C≡CH, —C(O)O$CH_3$, —CH(OAc)$CH_3$, —CN, —$CH_2$CN, —$CH_2X$ (wherein X is F, Br, Cl or I), —$CHX_2$ (wherein each X is F, Br or Cl) and methoxiran. In some aspects, $R^1$ is F. In some such embodiments, $R^2$ is F. In some such embodiments, $R^3$ is F. In other aspects, $R^1$ and $R^2$ are each F. In some such embodiments, $R^2$ and $R^{2a}$ are each F. In some aspects, each of $R^1$, $R^3$, and $R^4$ are independently selected from the group consisting of —OH, a hydrolyzable ester group, and a hydrolyzable ether group; each of $R^{2a}$ and $R^{3a}$ is hydrogen, $R^2$ is F, and and $R^5$ is selected from the group consisting of —$CH_3$, —CH=C=$CH_2$, —C≡CH, —C≡$CCH_3$, —$CH_2$C≡CH, —C(O)O$CH_3$, —CH(OAc)$CH_3$, —CN, —$CH_2$CN, —$CH_2X$ (wherein X is F, Br, Cl or I), —$CHX_2$ (wherein each X is F, Br or Cl) and methoxiran. In some such aspects, $R^5$ is —$CH_3$.

The fucose analog can have (I) or (II), or a pharmaceutically acceptable salt or solvate form thereof, wherein each of $R^1$-$R^4$ is independently selected from the group consisting of fluoro, chloro, —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), —OC(O)$C_2$-$C_{10}$ alkynylene(heterocycle), —OC(O)$CH_2O(CH_2CH_2O)_nCH_3$, —OC(O)$CH_2CH_2O(CH_2CH_2O)_nCH_3$, —O-tri-$C_1$-$C_3$ alkyl silyl, —O$C_1$-$C_{10}$ alkyl, —O$CH_2OC(O)$ alkyl, —O$CH_2OC(O)$ aryl, —O$CH_2OC(O)O$ alkyl, and —O$CH_2OC(O)O$ aryl, wherein each n is an integer independently selected from 0-5; each of $R^{2a}$ and $R^{3a}$ is independently selected from the group consisting of H, F, and Cl; and $R^5$ is selected from the group consisting of —$CH_3$, —CH=C=$CH_2$, —C≡CH, —C≡$CCH_3$, —$CH_2$C≡CH, —C(O)O$CH_3$, —CH(OAc)$CH_3$, —CN, —$CH_2$CN, —$CH_2X$ (wherein X is F, Br, Cl or I), —$CHX_2$ (wherein each X is F, Br or Cl) and methoxiran. In some aspects, $R^1$ is F. In some aspects, $R^2$ is F. In some aspects, $R^3$ is F. In some aspects, $R^1$ and $R^2$ are each F. In some aspects, $R^2$ and $R^{2a}$ are each F. In some aspects, $R^1$, $R^3$ and $R^4$ are each independently selected from —OH and —OC(O)$C_1$-$C_{10}$ alkyl; $R^2$ is F; and $R^5$ is —$CH_3$. In some such embodiments, $R^1$, $R^3$ and $R^4$ are each independently selected from —OH and —OAc; $R^2$ is F; and $R^5$ is —$CH_3$. In some aspects, $R^1$, $R^3$ and $R^4$ are each independently selected from —OH and —OC(O)$C_1$-$C_{10}$ alkyl; $R^2$ is F; $R^{2a}$ and $R^{3a}$ are each H; and $R^5$ is —$CH_3$. In some aspects, $R^1$, $R^3$ and $R^4$ are each independently selected from —OH and —OAc; $R^2$ is F; $R^{2a}$ and $R^{3a}$ are each H; and $R^5$ is —$CH_3$. In some aspects, $R^1$, $R^2$, $R^3$ and $R^4$ are each independently selected from —OH and —OC(O)$C_1$-$C_{10}$ alkyl; $R^{2a}$ and $R^{3a}$ are each H; and $R^5$ is —$CHF_2$. In some aspects, $R^1$, $R^2$, $R^3$ and $R^4$ are each independently selected from —OH and —OAc; $R^{2a}$ and $R^{3a}$ are each H; and $R^5$ is —CHF$_2$. In aspects, $R^1$, $R^2$, $R^3$ and $R^4$ are each independently selected from —OH and —OC(O)C$_1$-C$_{10}$ alkyl; $R^{2a}$ and $R^{3a}$ are each H; and $R^5$ is —CH$_2$F. In some aspects, $R^1$, $R^2$, $R^3$ and $R^4$ are each independently selected from —OH and —OAc; $R^{2a}$ and $R^{3a}$ are each H; and $R^5$ is —CH$_2$F.

The fucose analog can have formula (I) or (II), or a pharmaceutically acceptable salt or solvate form thereof, wherein $R^1$, $R^3$ and $R^4$ are each independently selected from OH, —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O) heterocycle, —OC(O)C$_1$-C$_{10}$ alkylene(aryl), —OC(O)C$_2$-C$_{10}$ alkenylene(aryl), —OC(O)C$_2$-C$_{10}$ alkynylene(aryl), —OC(O)C$_1$-C$_{10}$ alkylene(heterocycle), —OC(O)C$_2$-C$_{10}$ alkenylene(heterocycle), —OC(O)C$_2$-C$_{10}$ alkynylene(heterocycle), —OC(O)CH$_2$O(CH$_2$CH$_2$O)CH$_3$, —OC(O)CH$_2$CH$_2$O(CH$_2$CH$_2$O)$_n$CH$_3$, —O-tri-C$_1$-C$_3$ alkyl silyl, —OC$_1$-C$_{10}$ alkyl, —OCH$_2$OC(O) alkyl, —OCH$_2$OC(O) aryl, —OCH$_2$OC(O)O alkyl, and —OCH$_2$OC(O)O aryl, wherein each n is an integer independently selected from 0-5; $R^2$ is F; $R^{2a}$ and $R^{3a}$ are each H; and $R^5$ is —CH$_3$ The fucose analog can have formula (I) or (II), or a pharmaceutically acceptable salt or solvate form thereof, wherein: each of $R^1$-$R^4$ is independently selected from the group consisting of —OH, a hydrolysable ester group and a hydrolysable ether group or $R^1$-$R^4$ is independently selected from the group consisting of —OH, —OC(O)H, —OC(O)C$_1$-C$_{10}$ alkyl, —OC(O)aryl, —OC(O)heterocycle, —OC(O)C$_1$-C$_{10}$ alkylene(aryl), —OC(O)C$_1$-C$_{10}$ alkylene(heterocycle), —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-C$_1$-C$_3$ silyl, —OC$_1$-C$_{10}$ alkyl, —OCH$_2$OC(O) alkyl, —OCH$_2$OC(O)O alkyl, —OCH$_2$OC(O) aryl, and —OCH$_2$OC(O)O aryl, wherein each n is an integer independently selected from 0-5; each of $R^{2a}$ and $R^{3a}$ is hydrogen; and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is F, Br, Cl or I), —CHX$_2$ (wherein each X is F, Br or Cl), and methoxiran. In some aspects, $R^5$ is selected from the group consisting of —C≡CH, —C≡CCH$_3$, —C(O)OCH$_3$, —CH(OAc)CH$_3$, —CH$_2$CN, CHF$_2$, and —CH$_2$Br.

The fucose analog can have formula (I) or (II), or a pharmaceutically acceptable salt or solvate form thereof, wherein each of $R^1$-$R^4$ is independently selected from the group consisting of —OH, —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-C$_{10}$ alkenylene(aryl), —OC(O)C$_2$-C$_{10}$ alkynylene(aryl), —OC(O)C$_1$-C$_{10}$ alkylene(heterocycle), —OC(O)C$_2$-C$_{10}$ alkenylene(heterocycle), and —OC(O)C$_2$-C$_{10}$ alkynylene(heterocycle); and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is F, Br, Cl or I), —CHX$_2$ (wherein each X is F, Br or Cl), and methoxiran. $R^{2a}$ and $R^{3a}$ are as defined herein. In some aspects, each of $R^{2a}$ and $R^{3a}$ is independently selected from the group consisting of H, F, and Cl. In some aspects wherein each of $R^{2a}$ and $R^{3a}$ is hydrogen, $R^5$ is selected from the group consisting of —C≡CH, —C≡CCH$_3$, —C(O)OCH$_3$, —CH(OAc)CH$_3$, —CH$_2$CN, and —CH$_2$Br.

The fucose analog can have formula (I) or (II), or a pharmaceutically acceptable salt or solvate form thereof, wherein each of $R^1$-$R^4$ is independently selected from the group consisting of —OCH$_2$OC(O) alkyl, —OCH$_2$OC(O) alkenyl, —OCH$_2$OC(O) alkynyl, —OCH$_2$OC(O) aryl, —OCH$_2$OC(O) heterocycle, —OCH$_2$OC(O)O alkyl, —OCH$_2$OC(O)O alkenyl, —OCH$_2$OC(O)O alkynyl, —OCH$_2$OC(O)O aryl, and —OCH$_2$OC(O)O heterocycle; and $R^5$ is selected from the group consisting of —C≡CH, —C≡CCH$_3$, —CH$_2$C≡CH, C(O)OCH$_3$, —CH(OAc)CH$_3$, —CN, —CH$_2$CN, —CH$_2$X (wherein X is F, Br, Cl or I), —CHX$_2$ (wherein each X is F, Br or Cl), and methoxiran. $R^{2a}$ and $R^{3a}$ are as defined herein. In some aspects, each of $R^{2a}$ and $R^{3a}$ is independently selected from the group consisting of H, F, and Cl. In some aspects wherein each of $R^{2a}$ and $R^{3a}$ is hydrogen, $R^5$ is selected from the group consisting of —C≡CH, —C≡CCH$_3$, —C(O)OCH$_3$, —CH(OAc)CH$_3$, —CH$_2$CN, CHF$_2$, and —CH$_2$Br.

The fucose analog can have formula (I) or (II), or a pharmaceutically acceptable salt or solvate form thereof, wherein each of $R^1$-$R^4$ is independently selected from the group consisting of —OH, —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-C$_{10}$ alkenylene(aryl), —OC(O)C$_2$-C$_{10}$ alkynylene(aryl), —OC(O)C$_1$-C$_{10}$ alkylene(heterocycle), —OC(O)C$_2$-C$_{10}$ alkenylene(heterocycle), and —OC(O)C$_2$-C$_{10}$ alkynylene(heterocycle); and $R^5$ is selected from the group consisting of —C≡CH, —C≡CCH$_3$, —CH$_2$C≡CH, —C(O)OCH$_3$, —CH(OAc)CH$_3$, —CN, —CH$_2$CN, and methoxiran. $R^{2a}$ and $R^{3a}$ are as defined herein. In some aspects, each of $R^{2a}$ and $R^{3a}$ is independently selected from the group consisting of H, F, and Cl. In some aspects wherein each of $R^{2a}$ and $R^{3a}$ is hydrogen, $R^5$ is selected from the group consisting of —C≡CH, —C≡CCH$_3$, —C(O)OCH$_3$, —CH(OAc)CH$_3$, and —CH$_2$CN.

The fucose analog can have formula (I) or (II), or a pharmaceutically acceptable salt or solvate form thereof, wherein each of $R^1$-$R^4$ is independently selected from the group consisting of —OH, —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-C$_{10}$ alkenylene(aryl), —OC(O)C$_2$-C$_{10}$ alkynylene(aryl), —OC(O)C$_1$-C$_{10}$ alkylene(heterocycle), —OC(O)C$_2$-C$_{10}$ alkenylene(heterocycle), and —OC(O)C$_2$-C$_{10}$ alkynylene(heterocycle); and $R^5$ is selected from the group consisting of —CH$_2$F, —CH$_2$I, —CH$_2$Br, and —CH$_2$Cl. $R^{2a}$ and $R^{3a}$ are as defined herein. In some aspects, each of $R^{2a}$ and $R^{3a}$ is independently selected from the group consisting of H, F, and Cl. In some aspects wherein each of $R^{2a}$ and $R^{3a}$ is hydrogen, $R^5$ is —CH$_2$Br.

The fucose analog can have formula (I) or (II), or a pharmaceutically acceptable salt or solvate form thereof, wherein each of $R^1$-$R^4$ is independently selected from the group consisting of —OH, —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-

$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —CHF$_2$, —CHBr$_2$, and —CHCl$_2$. $R^{2a}$ and $R^{3a}$ are as defined herein. In some such embodiments, each of $R^{2a}$ and $R^{3a}$ is independently selected from the group consisting of H, F, and Cl.

The fucose analog can have formula (I) or (II), or a pharmaceutically acceptable salt or solvate form thereof, wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡CCH$_3$ and —CH$_2$C≡CH. $R^{2a}$ and $R^{3a}$ are as defined herein. In some aspects, each of $R^{2a}$ and $R^{3a}$ is independently selected from the group consisting of H, F, and Cl. In some aspects wherein each of $R^{2a}$ and $R^{3a}$ is hydrogen, $R^5$ is selected from the group consisting of —C≡CH, and —C≡CCH$_3$.

The fucose analog can have formula (I) or (II), or a pharmaceutically acceptable salt or solvate form thereof, wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡CCH$_3$, —(CH$_2$)$_n$(CN) (where n=0 or 1) and —CO(O)CH$_3$. $R^{2a}$ and $R^{3a}$ are as defined herein. In some aspects, each of $R^{2a}$ and $R^{3a}$ is independently selected from the group consisting of H, F, and Cl. In some aspects wherein each of $R^{2a}$ and $R^{3a}$ is hydrogen, $R^5$ is selected from the group consisting of —C≡CH, —C≡CCH$_3$, and —C(O)OCH$_3$.

The fucose analog can have formula (I) or (II), or a pharmaceutically acceptable salt or solvate form thereof, wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡CCH$_3$, —CH$_2$CN and —CO(O)CH$_3$. $R^{2a}$ and $R^{3a}$ are as defined herein. In some aspects, each of $R^{2a}$ and $R^{3a}$ is independently selected from the group consisting of H, F, and Cl.

The fucose analog can have formula (I) or (II), or a pharmaceutically acceptable salt or solvate form thereof, wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), and —OC(O)$C_2$-$C_{10}$ alkynylene(heterocycle); and $R^5$ is selected from the group consisting of —C≡CH, —C≡CCH$_3$, —CH(OAc)CH$_3$, —CH$_2$CN, and —CO(O)CH$_3$. $R^{2a}$ and $R^{3a}$ are as defined herein. In some aspects, each of $R^{2a}$ and $R^{3a}$ is independently selected from the group consisting of H, F, and Cl.

The fucose analog can have formula (I) or (II), or a pharmaceutically acceptable salt or solvate form thereof, wherein $R^1$, $R^3$ and $R^4$ are each independently selected from the group consisting of OH, a hydrolyzable ester, or a hydrolyzable ether or $R^1$, $R^3$ and $R^4$ are each independently selected from the group consisting of OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), —OC(O)$C_2$-$C_{10}$ alkynylene(heterocycle), —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-$C_1$-$C_3$ alkyl silyl, —O$C_1$-$C_{10}$ alkyl, —OCH$_2$OC(O) alkyl, —OCH$_2$OC(O) aryl, —OCH$_2$OC(O)O alkyl, and —OCH$_2$OC(O)O aryl, wherein each n is an integer independently selected from 0-5; $R^2$ is F; $R^{2a}$ and $R^{3a}$ are each H; and $R^5$ is —CH$_3$.

The fucose analog can have formula (I) or (II), or a pharmaceutically acceptable salt or solvate form thereof, wherein $R^1$, $R^2$, $R^3$ and $R^4$ are each independently selected from the group consisting of OH, a hydrolyzable ester, or a hydrolyzable ether or $R^1$, $R^2$, $R^3$ and $R^4$ are each independently selected from OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkenylene(aryl), —OC(O)$C_2$-$C_{10}$ alkynylene(aryl), —OC(O)$C_1$-$C_{10}$ alkylene(heterocycle), —OC(O)$C_2$-$C_{10}$ alkenylene(heterocycle), —OC(O)$C_2$-$C_{10}$ alkynylene(heterocycle), —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-$C_1$-$C_3$ alkyl silyl, —O$C_1$-$C_{10}$ alkyl, —OCH$_2$OC(O) alkyl, —OCH$_2$OC(O) aryl, —OCH$_2$OC(O)O alkyl, and —OCH$_2$OC(O)O aryl, wherein each n is an integer independently selected from 0-5; $R^{2a}$ and $R^{3a}$ are each H; and $R^5$ is —C≡CH.

The any of the embodiments provided herein, the fucose analog can have formula (I) or (II), or a pharmaceutically acceptable salt or solvate form thereof, wherein $R^5$, $R^{2a}$, and $R^{3a}$ are as defined herein, and each of $R^1$-$R^4$ is hydroxyl or —OC(O)$C_1$-$C_{10}$ alkyl.

The fucose analog can have formula (I) or (II), or a pharmaceutically acceptable salt or solvate form thereof, wherein $R^5$, $R^{2a}$, and $R^{3a}$ are as defined herein, and each of $R^1$-$R^4$ is hydroxyl or —OAc.

The fucose analog can have formula (I) or (II), or a pharmaceutically acceptable salt or solvate form thereof, wherein each of $R^1$-$R^4$ is independently selected from the group consisting of —OH, and —OC(O)$C_1$-$C_{10}$ alkyl; and $R^5$ is selected from the group consisting of —C≡CH, —C≡CCH$_3$, —CH(OAc)CH$_3$, —CH$_2$CN, —CO(O)CH$_3$, —CH$_2$F and —CHF$_2$ or $R^5$ is selected from the group consisting of —C≡CH, —C≡CCH$_3$, —CH(OAc)CH$_3$, —CH$_2$CN, —CO(O)CH$_3$, CHF$_2$, and —CH$_2$Br. $R^{2a}$ and $R^{3a}$ are as defined herein. In some aspects, each of $R^{2a}$ and $R^{3a}$ is independently selected from the group consisting of H, F, and Cl. In other aspects, each of $R^{2a}$ and $R^{3a}$ is H.

The fucose analog can have formula (I) or (II), or a pharmaceutically acceptable salt or solvate form thereof, wherein each of $R^1$-$R^4$ is independently selected from the group consisting of —OH, and —OAc; and $R^5$ is selected from the group consisting of —C≡CH, —C≡CCH$_3$, —CH(OAc)CH$_3$, —CH$_2$CN, —CO(O)CH$_3$, —CH$_2$F and —CHF$_2$ or $R^5$ is selected from the group consisting of —C≡CH, —C≡CCH$_3$, —CH(OAc)CH$_3$, —CH$_2$CN, —CO(O)CH$_3$, —CHF$_2$, and —CH$_2$Br. R$^{2a}$ and R$^{3a}$ are as defined herein. In some aspects, each of R$^{2a}$ and R$^{3a}$ is independently selected from the group consisting of H, F, and Cl. In other aspects, each of R$^{2a}$ and R$^{3a}$ is H.

The fucose analog can have formula (I) or (II), or a pharmaceutically acceptable salt or solvate form thereof, wherein each of R$^1$-R$^4$ is independently selected from the group consisting of —OH, and —OC(O)C$_1$-C$_{10}$ alkyl; and R$^5$ is selected from the group consisting of —C≡CH, —CH$_2$F and —CHF$_2$. R$^{2a}$ and R$^{3a}$ are as defined herein. In some aspects, each of R$^{2a}$ and R$^{3a}$ is independently selected from the group consisting of H, F, and Cl. In other aspects, each of R$^{2a}$ and R$^{3a}$ is H.

The fucose analog can have formula (I) or (II), or a pharmaceutically acceptable salt or solvate form thereof, wherein each of R$^1$-R$^4$ is independently selected from the group consisting of —OH, and —OAc; and R$^5$ is selected from the group consisting of —C≡CH, —CH$_2$F and —CHF$_2$. R$^{2a}$ and R$^{3a}$ are as defined herein. In some aspects, each of R$^{2a}$ and R$^{3a}$ is independently selected from the group consisting of H, F, and Cl. In other aspects, each of R$^{2a}$ and R$^{3a}$ is H.

The fucose analog can have formula (I) or (II), or a pharmaceutically acceptable salt or solvate form thereof, wherein each of R$^1$-R$^4$ is independently selected from the group consisting of —OH, and —OC(O)C$_1$-C$_{10}$ alkyl; and R$^5$ is —C≡CH. R$^{2a}$ and R$^{3a}$ are as defined herein.

The fucose analog can have formula (I) or (II), or a pharmaceutically acceptable salt or solvate form thereof, wherein each of R$^1$-R$^4$ is independently selected from the group consisting of —OH, and —OAc; and R$^5$ is —C≡CH. R$^{2a}$ and R$^{3a}$ are as defined herein. In some such embodiments, R$^{2a}$ and R$^{3a}$ are hydrogen.

The fucose analog can formula (I) or (II), or a pharmaceutically acceptable salt or solvate form thereof, wherein each of R$^1$-R$^4$ is independently selected from the group consisting of —OH, and —OC(O)C$_1$-C$_{10}$ alkyl; and R$^5$ is CHF$_2$. R$^{2a}$ and R$^{3a}$ are as defined herein. In some such embodiments, R$^{2a}$ and R$^{3a}$ are hydrogen.

The fucose analog can have formula (I) or (II), or a pharmaceutically acceptable salt or solvate form thereof, wherein each of R$^1$-R$^4$ is independently selected from the group consisting of —OH, and —OAc; and R$^5$ is —CHF$_2$. R$^{2a}$ and R$^{3a}$ are as defined herein. In some such embodiments, R$^{2a}$ and R$^{3a}$ are hydrogen.

The fucose analog can have formula (I) or (II), or a pharmaceutically acceptable salt or solvate form thereof, wherein each of R$^1$-R$^4$ is —OH or an ester selected from the group consisting of —OC(O)H, —OC(O)C$_1$-C$_{10}$ alkyl, —OC(O)C$_2$-C$_{10}$ alkenyl, —OC(O)C$_2$-C$_{10}$ alkynyl, —OC(O)aryl, —OC(O)heterocycle, —OC(O)C$_1$-C$_{10}$ alkylene(aryl), —OC(O)C$_2$-C$_{10}$ alkenylene(aryl), —OC(O)C$_2$-C$_{10}$ alkynylene(aryl), —OC(O)C$_1$-C$_{10}$ alkylene(heterocycle), —OC(O)C$_2$-C$_{10}$ alkenylene(heterocycle), —OC(O)C$_2$-C$_{10}$ alkynylene(heterocycle), —OC(O)CH$_2$O(CH$_2$CH$_2$O)$_n$CH$_3$ (where n is 0-5), and —OC(O)CH$_2$CH$_2$O(CH$_2$CH$_2$O)$_n$CH$_3$ (where n is 0-5); and R$^5$ is selected from the group consisting of —C≡CH, —C≡CCH$_3$, —CH$_2$C≡CH, —C(O)OCH$_3$, —CH(OAc)CH$_3$, —CN, —CH$_2$CN, —CH$_2$X (wherein X is F, Br, Cl or I), —CHX$_2$ (wherein each X is F, Br or Cl), and methoxiran. R$^{2a}$ and R$^{3a}$ are as defined herein. In some aspects wherein each of R$^{2a}$ and R$^{3a}$ is hydrogen, R$^5$ is selected from the group consisting of —C≡CH, —C≡CCH$_3$, —C(O)OCH$_3$, —CHF$_2$—CH(OAc)CH$_3$, —CH$_2$CN, and —CH$_2$Br.

The fucose analog can have formula (I) or (II), or a pharmaceutically acceptable salt or solvate form thereof, wherein each of R$^1$-R$^4$ is independently selected from the group consisting of —OH, and —OC(O)C$_1$-C$_{10}$ alkyl; and R$^5$ is —CH$_2$X (wherein X is F, Br, Cl or I). R$^{2a}$ and R$^{3a}$ are as defined herein. In some aspects, R$^{2a}$ and R$^{3a}$ are each independently selected from the group consisting of H, F, and Cl.

The fucose analog can have formula (I) or (II), or a pharmaceutically acceptable salt or solvate form thereof, wherein each of R$^1$-R$^4$ is independently selected from the group consisting of —OH, and —OAc; and R$^5$ is —CH$_2$X (wherein X is F, Br, Cl or I). R$^{2a}$ and R$^{3a}$ are as defined herein. In some aspects, R$^{2a}$ and R$^{3a}$ are each independently selected from the group consisting of H, F, and Cl. In some aspects, R$^{2a}$ and R$^{3a}$ are each H.

The fucose analog can have formula (I) or (II), or a pharmaceutically acceptable salt or solvate form thereof, wherein each of R$^1$-R$^4$ is independently selected from the group consisting of —OH, and —OC(O)C$_1$-C$_{10}$ alkyl; and R$^5$ is —CH$_2$Br. R$^{2a}$ and R$^{3a}$ are as defined herein. In some aspects, R$^{2a}$ and R$^{3a}$ are each independently selected from the group consisting of H, F, and Cl.

The fucose analog can have formula (I) or (II), or a pharmaceutically acceptable salt or solvate form thereof, wherein each of R$^1$-R$^4$ is independently selected from the group consisting of —OH, and —OAc; and R$^5$ is —CH$_2$Br. R$^{2a}$ and R$^{3a}$ are as defined herein. In some aspects, R$^{2a}$ and R$^{3a}$ are each independently selected from the group consisting of H, F, and Cl.

In some embodiments, the fucose analog has a molecular weight of less than 2000 daltons. In some embodiments, the fucose analog has a molecular weight of less than 1000 daltons.

In some embodiments, R$^5$ is not substituted.
In some embodiments, each of R$^1$-R$^4$ is not substituted.
In some embodiments, R$^5$ is not a ketone (—C(O)alkyl).
In some embodiments, R$^5$ is not —H(CH$_3$)OAc.
In some embodiments, R$^5$ is not —CH(CH$_3$)OAc, when each of R$^1$-R$^4$ is —OAc.
In some embodiments, R$^5$ is not —C≡CH.
In some embodiments, R$^5$ is not —C≡CH, when any of R$^1$-R$^4$ is —OAc.
In some embodiments, R$^5$ is not —C≡CH, when any of R$^1$-R$^4$ is OC(O)alkyl.
In some embodiments, R$^5$ is not —C≡CH, when each of R$^1$-R$^4$ is OC(O)alkyl.
In some embodiments, R$^5$ is not —C≡CH$_3$ when each of R$^1$-R$^4$ is OH.
In some embodiments, when R$^5$ is other than —CH=C=CH$_2$, —CH$_2$F or —CHF$_2$, at least one of R$^1$, R$^2$, R$^3$, R$^{2a}$ and R$^{3a}$ is fluoro or chloro.

In some embodiments, the fucose analog is alkynyl fucose peracetate. In some embodiments, the fucose analog is alkynyl fucose triacetate. In some embodiments, the fucose analog is alkynyl fucose diacetate. In some embodiments, the fucose analog is mixture of alkynyl fucose peracetate, alkynyl fucose triacetate and alkynyl fucose diacetate.

In some embodiments, the fucose analog is mixture of alkynyl fucose peracetate, alkynyl fucose triacetate, alkynyl fucose diacetate and alkynyl fucose monoacetate.

In any of the various embodiments, the fucose analog is not fucose. In some embodiments, the fucose analog is not alkynyl fucose peracetate. In some embodiments, the fucose analog is not galactose or L-galactose.

In some embodiments of formulae (I) and (II), R$^{2a}$ and R$^{3a}$ are each hydrogen.

In some embodiments of formulae (I) and (II), $R^5$ is selected from the group consisting of —$CH_3$, —$CH_2CH_3$, —$CH_2C\equiv CH$, —$CH=CHCH_3$, -cyclopropyl, -oxirane, -oxirane substituted with methyl, —$CH_2F$, —$CH_2Cl$, —$CH_2Br$, —$CH_2I$, —$CHF_2$, —$CH=C=CH_2$, —$CH_2N_3$ and —$CH_2CH_2N_3$.

In some embodiments of formulae (I) and (II), the small electron withdrawing group is selected from fluoro, chloro, bromo, —$CHF_2$, —$CH=C=CH_2$, —$C\equiv CH$, —$C\equiv CCH_3$, —$CH_2C\equiv CH$, —$CO_2H$, —C(O)—$OC_1$-$C_4$ alkyl, —CH(OAc)$CH_3$, —CN, —$CH_2CN$, —$CH_2X$ (wherein X is Br, Cl or I), and methoxiran.

In some embodiments of formulae (I) and (II), $R^5$ is selected from the group consisting of —$CH_3$, —$C\equiv CH$, —$CH_2F$, —$CH_2Br$, and —$CHF_2$. In some further embodiments, each of $R^1$, $R^2$, $R^{2a}$, $R^3$, $R^{3a}$ and $R^4$ is independently selected from the group consisting of —OH, —OC(O)H, and —OC(O)$C_1$-$C_{10}$ alkyl.

In some embodiments of formulae (I) and (II), the small electron withdrawing group is selected from fluoro, chloro, bromo, —$CHF_2$, —$CH=C=CH_2$, —$C\equiv CH$, —$C\equiv CCH_3$, —$CH_2C\equiv CH$, —$CO_2H$, —C(O)$OC_1$-$C_4$ alkyl, —CH(OAc)$CH_3$, —CN, —$CH_2CN$, —$CH_2X$ (wherein X is Br, Cl or I), and methoxiran.

In some embodiments of formulae (I) and (II), at least two of $R^1$, $R^2$, $R^{2a}$, $R^3$, $R^{3a}$ and $R^4$ are independently selected small electron withdrawing groups.

In any of the various embodiments, each of formulae (I) and (II) can be the alpha or beta anomer of the corresponding aldose form.

In some aspects, exemplary fucose analogs for use in the present invention include those that have been shown to have an inhibitory effect on antibody core fucosylation at concentrations of 50 uM or 1 mM, particularly those that have shown an inhibitory effect of greater than about 80% at 50 uM or 1 mM (see Tables 1 and 2 below). Methods of determining whether a fucose analog is capable of having an effect on antibody core fucosylation is provided in WO 2012/019165.

TABLE 1

| Name (Chemical name) | $R^5$ | $R^1$-$R^4$ | Inhibition at 50 μM | Inhibition at 1 mM |
|---|---|---|---|---|
| Alkynyl fucose (5-ethynylarabinose) | —$C\equiv CH$ | —OH | >80% | ND |
| Alkynyl fucose peracetate Alkynyl fucose tetraacetate (5-ethynylarabinose tetraacetate) | —$C\equiv CH$ | —OAc | >80% | >80% |
| 5-propynyl fucose tetraacetate (5-propynylarabinose tetraacetate) | —$C\equiv CH_3$ | —OAc | 50% | >80% |
| propargyl fucose tetraacetate ((3S,4R,5R,6S)-6-(prop-2-ynyl)-tetrahydro-2H-pyran-2,3,4,5-tetrayl tetraacetate) | —$CH_2C\equiv CH$ | —OAc | ~10% | ~10-20% |
| Peracetyl galactose (galactose pentaacetate) | —OAc | —OAc | ~0% | ~0% |
| 5-vinyl fucose tetraacetate (5-ethylenylarabinose tetraacetate) | —$CHCH_2$ | —OAc | ~0% | ~4% |
| 6-cyano fucose tetraacetate (6-cyanofucose tetraacetate) | —$CH_2CN$ | —OAc | 30% | >80% |
| 5-cyano fucose tetraacetate (pyranose form) (5-cyanoarabinopyranose tetraacetate) | —CN | —OAc | 20% | ND |
| 5-cyano fucose tetraacetate (furanose form) (5-cyanoarabinofuranose tetraacetate) | —CN | —OAc | 5-10% | ND |
| 5-methylester fucose tetraacetate (5-carboxymethyl arabinose tetraacetate) | —C(O)OCH$_3$ | —OAc | 30% | >80% |
| 5-(CH(OAc)CH$_3$) peracetyl fucose (6-methylgalactose pentaacetate) | —CH(OAc)CH$_3$ | —OAc | ~0% | 40% |
| 5-methyloxiran-arabinose tetraacetate ((3S,4R,5S,6R)-6-((S)-2-methyloxiran-2-yl)-tetrahydro-2H-pyran-2,3,4,5-tetrayl tetraacetate) | methyloxiranyl | —OAc | ~0% | ~35-40% |
| 6-iodo-fucose tetraacetate (6-iodofucose tetraacetate) | —$CH_2I$ | —OAc | 3% | 30% |
| 6-chloro-fucose tetraacetate (6-chlorofucose tetraacetate) | —$CH_2Cl$ | —OAc | 20% | 20-30% |
| 6-bromo-fucose tetraacetate (6-bromofucose tetraacetate) | —$CH_2Br$ | —OAc | 50% | 80% |
| Alkynyl fucose tetrapropanonate (5-ethynylarabinose tetrapropanoate) | —$C\equiv CH$ | —OC(O)$CH_2$—$CH_3$ | >80% | >80% |

TABLE 1-continued

| Name (Chemical name) | $R^5$ | $R^1$-$R^4$ | Inhibition at 50 μM | Inhibition at 1 mM |
|---|---|---|---|---|
| Alkynyl fucose tetra-n-hexanoate (5-ethynylarabinose tetrahexanoate) | —C≡CH | —OC(O)(CH$_2$)$_4$—CH$_3$ | >80% | >80% |
| Alkynyl fucose tetrakis(trimethylacetate) (5-ethynylarabinose tetra(trimethylacetate)) | —C≡CH | —OC(O)C(CH$_3$)$_3$ | 20% | 60% |
| Alkynyl fucose tetrakis(trimethylacetate) (5-ethynylarabinose tetra(trimethylacetate)) | —C≡CH | —OC(O)C(CH$_3$)$_3$ | 5% | 10% |
| Alkynyl fucose 1,2,3-(trimethylacetate) (5-ethynylarabinose 1,2,3-(trimethylacetate)) | —C≡CH | —OC(O)C(CH$_3$)$_3$ and —OH | ~0% | ND |
| Alkynyl fucose di(trimethylacetate) (5-ethynylarabinose 1,3-(trimethylacetate)) | —C≡CH | —OC(O)C(CH$_3$)$_3$ and —OH | >80% | ND |
| Alkynyl fucose pernicotinate | —C≡CH | —C(O)-3-pyridyl | >80% | >80% |
| Alkynyl fucose perisonicotinate | —C≡CH | —C(O)-4-pyridyl | >80% | >80% |
| Alkynyl fucose per-PEG ester | —C≡CH | —C(O)—(CH$_2$CH$_2$O)$_2$—OCH$_3$ | >80% | >80% |
| 1-methyl-2,3,4-triacetyl alkynyl fucose | —C≡CH | $R^1$ = OCH$_3$ $R^2$, $R^3$, $R^4$ = OAc | 68% | >80% |
| Alkynyl fucose perisobutanoate | —C≡CH | —OC(O)CH(CH$_3$)$_2$ | >80% | >80% |

"ND" means not detected due to poor antibody production or inhibition of cell growth in the presence of the fucose analog.

TABLE 2

| Name (Chemical name) | $R^5$ | $R^1$ | $R^2$/$R^{2a}$ | $R^3$/$R^{3a}$ | Inhibition at 50 μM | Inhibition at 1 mM |
|---|---|---|---|---|---|---|
| 2-deoxy-2-fluorofucose diacetate ($R^4$ = OAc) | —CH$_3$ | —OH | —F/—H | —OAc/—H | >80% | >80% |
| 2-deoxy-2-chlorofucose triacetate ($R^4$ = OAc) | —CH$_3$ | —OAc | —Cl/—H | —OAc/—H | 17% | >80% |
| Allene ($R^4$ = OAc) | —CH=C=CH$_2$ | —OAc | —OAc/—H | —OAc/—H | 23% | 34% |
| 2-deoxy-2-fluorofucose ($R^4$ = OH) (also referred to as 2-fluorofucose) | —CH$_3$ | —OH | —F/—H | —OH/—H | >80% | >80% |
| 2-deoxy-2-fluorofucose peracetate ($R^4$ = OAc) | —CH$_3$ | —OAc | —F/—H | —OAc/—H | >80% | >80% |
| 1,2-difluoro-1,2-didexoy fucose peracetate ($R^4$ = OAc) | —CH$_3$ | —F | —F/—H | —OAc/—H | >80% | >80% |
| 6,6-difluorofucose tetraacetate ($R^4$ = OAc) | —CHF$_2$ | —OAc | —OAc/—H | —OAc/—H | >80% | >80% |
| 2-deoxy-2,2-difluorofucopyranose triacetate (alpha) ($R^4$ = OAc) | —CH$_3$ | —OAc | —F/—F | —OAc/—H | 0 | 64% |
| 2-deoxy-2,2-difluorofucopyranose triacetate (beta) ($R^4$ = OAc) | —CH$_3$ | —OAc | —F/—F | —OAc/—H | 0 | 75% |
| 6-methyl-tetrahydro-2H-pyran-2,4,5-triyl triacetate ($R^4$ = OAc) | —CH$_3$ | —OAc | —H/—H | —OAc/—H | 0 | 36% |
| 5-Benzyloxy fucose peracetate ($R^4$ = OAc) | —CH$_2$OCH$_2$Ph | —OAc | —OAc/—H | —OAc/—H | 0 | 75% |

"ND" not detected due to poor antibody production or inhibition of cell growth in the presence of the fucose analog.

In some aspects, exemplary fucose analogs for use in the present invention include those that inhibit cell surface fucosylation of LS174t colon carcinoma cells as shown in FIGS. 1 to 3.

In any of the various embodiments, the endocylic ring oxygen of the fucose analog of formulae (I) and (II) can be replaced by sulfur.

Also provided herein are the pharmaceutically acceptable salt and solvate forms of the compounds of formulae I and II. Accordingly, in any of the various embodiments provided herein, the pharmaceutically acceptable salt or solvate forms of the disclosed compounds can be used. Solvates typically do not significantly alter the physiological activity of the compounds and as such may function as pharmacological equivalents. One type of solvate is a hydrate.

In some aspects, the fucose analog is soluble in formulation buffer (e.g. aqueous formulation buffer) at a concentration of at least 10 mM. In some embodiments, the fucose analog is soluble in formulation buffer at a concentration of at least 100 mM. In some aspects, the fucose analog is soluble in formulation buffer (e.g. aqueous formulation buffer) at a concentration of at least 100 µg/ml, at least 1 mg/ml, at least 50 mg/ml, at least about 100 mg/ml, at least about 200 mg/ml, or at least about 300 mg/ml.

In some aspects, the fucose analog that is administered to a subject is capable of being converted in vivo to a fucose analog having formula (I) or (II), or a pharmaceutically acceptable salt or solvate form thereof, wherein each of of $R^1$, $R^3$, and $R^4$ is —OH; each of $R^{2a}$ and $R^{3a}$ is independently selected from the group consisting of H, F, and Cl; $R^2$ is F, and $R^5$ is selected from the group consisting of —CH$_3$, —CH=C=CH$_2$, —C≡CH, —C≡CCH$_3$, —CH$_2$C≡CH, —C(O)OCH$_3$, —CH(OAc)CH$_3$, —CN, CH$_2$CN, —CH$_2$X (wherein X is F, Br, Cl or I), —CHX$_2$ (wherein each X is F, Br or Cl) and methoxiran. In some aspects, the fucose analog is capable of being converted in vivo to a fucose analog having formula (I) or (II), or a pharmaceutically acceptable salt or solvate form thereof, wherein each of of $R^1$, $R^3$, and $R^4$ is —OH; each of $R^{2a}$ and $R^{3a}$ is independently selected from the group consisting of H, F, and Cl; $R^2$ is F and $R^5$ is —CH$_3$.

In some aspects, the fucose analog that is administered to a subject is capable of being converted in vivo to 2-fluorofucose.

In some aspects, the fucose analog has the formula:

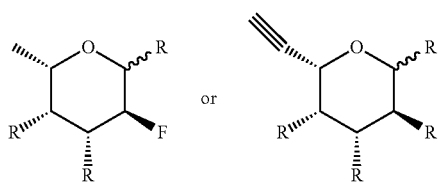

wherein each R is independently selected from —OH, or a hydrolyzable ester or ether group; or a pharmaceutically acceptable salt or solvate form thereof. In some such aspects, each R is independently selected from —OH, or —OC(O)C$_1$-C$_{10}$ alkyl. In some such aspects, each R is independently selected from —OH or —OC(O)CH$_3$. In some such aspects, each R is —OH.

Pharmaceutical Compositions

Fucose analogs of formulae (I) and (II), or pharmaceutically acceptable salt or solvate forms thereof, (hereinafter 'fucose analogs') can be formulated for use in animals, e.g., for the treatment of sickle cell disease, vascular obstruction, and/or inflammation. The fucose analogs can be formulated as pharmaceutical compositions comprising a therapeutically or prophylactically effective amount of the fucose analog and one or more pharmaceutically compatible (acceptable) ingredients. In some aspects, pharmaceutical compositions of fucose analogs and pharmaceutical excipients are provided in which an effective amount of a fucose analog(s) is in admixture with the excipients, suitable for administration to an animal. In preferred aspects, the fucose analog is formulated for administration to a human. According, the present invention provides a pharmaceutical composition comprising a fucose analog formulated for administration to a human. The formulated fucose analog will generally comprise one or more pharmaceutically compatible (acceptable) ingredients.

Exemplary pharmaceutical or non-pharmaceutical compositions typically include one or more carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable excipients include, for example, amino acids, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will typically contain a therapeutically effective amount of the fucose analog, typically in purified form, together with a suitable amount of carrier so as to provide the form for proper administration to the subject. The formulations correspond to the mode of administration.

The pharmaceutical compositions described herein can be in any form that allows for the composition to be administered to an animal (e.g., a mammal). The compositions can be in the form of a solid or liquid. Typical routes of administration include, without limitation, oral, parenteral, and sublingual. Parenteral administration includes subcutaneous injections, intraperitoneal injections, intravenous, intramuscular, intrasternal injection or infusion techniques. Preferably, the compositions are administered orally. These pharmaceutical compositions can be formulated so as to allow a fucose analog to be bioavailable upon administration of the composition to an animal. Compositions can also take the form of one or more dosage units, where for example, a tablet can be a single dosage unit, and a container of a fucose analog in solid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the fucose analog, the manner of administration, the composition employed, and the severity of the disease or condition being treated.

The pharmaceutically acceptable carrier or vehicle can be particulate, so that the compositions are, for example, in tablet or powder form. The carrier(s) can be liquid, with the compositions being, for example, an oral syrup, flavored water, or injectable liquid.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In some aspects, the composition is formulated into a powder and the end user mixes the power in an aqueous solution for oral administration. In a composition for administration by injection (as described above), one or more of a surfactant, preservative, wetting agent, dispersing agent, suspending agent, buffer, stabilizer and isotonic agent can also be included.

As noted above, the amount of the fucose analog that is effective in the methods described herein will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a fucose analog such that a suitable dosage will be obtained. Typically, this amount is at least about 0.01% of a fucose analog by weight of the composition. In some aspects, when intended for oral administration, this amount can be varied to range from about 0.1% to about 80% by weight of the composition. Preferred oral compositions can comprise, for example, from about 4% to 100%, 4% to 75% or from 4% to about 50% of the fucose analog by weight of the composition.

In some aspects, for intravenous administration, the amount administered will be in the range from about 1 to about 500 mg/kg of body weight of the fucose analog.

Generally, the oral dosage of fucose analog administered to an animal is about 1 mg/kg to about 1 g/kg of the animal's body weight, more typically about 5 mg/kg, 10 mg/kg, 20 mg/kg, 30 mg/kg, 40 mg/kg, or 50 mg/kg to about 1 g/kg of the animal's body weight. In some aspects, the dosage administered to an animal is about 1 g, about 5 g, or about 10 g to about 150 g per day, or from about 1 g, about 5 g, about 10 g, about 15 g or about 20 g to about 60 g per day.

Generally, a fucose analog or a pharmaceutical composition thereof can be administered on a daily, weekly, biweekly or monthly schedule, according to the desired effect. In some aspects, a fucose analog or a pharmaceutical composition thereof can be administered from about 1 to 5, about 1 to about 10, about 1 to about 15, or more cycles, wherein each cycle is a month in duration. The doses within each cycle can be given on daily (including once daily, twice daily, or more than twice daily), every other day, twice weekly, weekly, bi-weekly, once every three weeks or monthly basis. A cycle may optionally include a resting period. Alternatively, a resting period can be included between cycles. In some aspects, administration will be for the duration of the disease.

The preferred mode of administration of a fucose analog, or a pharmaceutical composition thereof, is left to the discretion of the practitioner, and will depend in-part upon the site of the medical condition. In one embodiment, the fucose analog or compositions are administered parenterally. In another embodiment, the fucose analog or compositions are administered orally.

In another embodiment, the fucose analogs can be delivered in a vesicle, in particular a liposome (see Langer, *Science* 249:1527-1533 (1990); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 317-327; see generally ibid.).

In yet another embodiment, the fucose analogs or compositions can be delivered in a controlled release system. In one embodiment, a pump can be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). Other controlled-release systems discussed in the review by Langer (*Science* 249:1527-1533 (1990)) can be used.

The term "carrier" refers to a diluent, adjuvant or excipient, with which a fucose analog is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the fucose analogs or compositions and pharmaceutically acceptable carriers are sterile. Water is a preferred carrier when the fucose analogs are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Therapeutic Methods

The fucose analogs are useful for treating vaso-occlusion, sickle cell disease as well as other chronic or acute inflammatory conditions. Exemplary fucose analogs inhibit the binding of adhesion molecules to cells, including white blood cells (e.g., neutrophils). In some aspects, the adhesion molecules are the selections, e.g., E-selectin, P-selectin, and L-selectin.

In some aspects, treatment with a fucose analog reduces the vaso-occlusive epidoses associated with sickle cell disease. In some aspects, treatment with a fucose analog inhibits leukocyte capture of red blood cells, including sickle red blood cells. In some aspects, treatment with a fucose analog inhibits leukocyte rolling along on the endothelium. In some aspects, treatment with a fucose analog inhibits cell adhesion to the endothelium, e.g., leukocyte adhesion to the endothelium. In some aspects, treatment with a fucose analog inhibits neutrophil extravasation.

The present methods can further comprise the administration of a fucose analog and a therapeutic agent or pharmaceutically acceptable salts or solvates thereof. The fucose analog and the therapeutic agent can act additively or, more preferably, synergistically. In a preferred embodiment, a composition comprising a fucose analog is administered concurrently with the administration of one or more therapeutic agent(s), which can be part of the same composition or in a different composition from that comprising the fucose analog. In another embodiment, a fucose analog is administered prior to or subsequent to administration of the therapeutic agent(s).

The invention is further described in the following examples, which are not intended to limit the scope of the invention.

EXAMPLES

Example 1: Exemplary Fucose Analogs Decrease Cell Surface Fucosylation

The effects of the fucose analogs on LS174t colon carcinoma cell line was examined. 150 µM of each analog was used under standard culture conditions for 8 days with regular changes of culture medium including fresh inhibitor. After the incubation period, the cells were analyzed by FACS using different detection reagents:
LCA, AAL, UEA-1, anti-sialyl Lewis$^x$ antibody (anti-CD15s), anti-Lewis$^x$ antibody (anti-SSEA1), an anti-Lewis$^y$ antibody (cBR96). The procedure involved washing of the cells with FACS buffer (PBS+2% fetal bovine serum+0.02% sodium azide) 3 times followed by incubation with the primary detection reagent for 1 hr at 4° C., followed by 3 washes with FACS buffer and then incubation with the secondary detection reagent for 1 hr at 4° C. The cells were finally washed with FACS buffer 3 times and resuspended in FACS buffer and examined using a BD FACScan instrument. The cell line examined showed staining with the different reagents. A decrease in staining demonstrates a decrease of fucose on the cell surface. See FIGS. 1, 2, and 3.

Example 2: 2-Fluorofucose Inhibits Cell Adhesion Interactions

LS174T cells (ATCC) were cultured in MEM-Eagle with 10% FBS with or without 100 µM 2-fluorofucose for 10 days. For adhesion to purified E-selectin, non-tissue culture treated 96-well clear bottom black culture plates were coated with E-selectin-Fc chimera (5 µg/mL, PBS) and controls with 3% BSA/PBS, 2 hr at 37° C., then overnight at 4° C. Wells were washed two times with PBS and blocked with 3% BSA/PBS (2 hr, room temperature). LS174T cells were harvested and washed with PBS 2 times, labeled with 5 µM Calcein-AM in serum-free medium (15 min), and washed with DBPS two times. Cells in DPBS (100 µL) of were added to each well and the plate was kept at 4° C. for 2 hr. Plates were read at 480 nm excitation and 520 nm emission (total cell reading) and then washed with DPBS four times, followed by fluorescent analysis.

For adhesion to activated HUVEC cells, non-tissue culture treated 96-well clear bottom black culture plates were coated with attachment factor (100 µL/well), 30 min at room temperature. Wells were aspirated and HUVECs were added to half of the wells (40,000 cells/200 µL cell culture medium) while 3% BSA/PBS was added to the remaining control wells (100 µL) and the plate was incubated overnight at 37° C., 5% $CO_2$. The confluent HUVEC cells were then treated with TNFα (20 ng/mL in PBS) for 4 hr at 37° C. Meanwhile tumor cells were labeled with Calcein-AM as described. The wells of the 96-well plate were all aspirated and seeded with 2-fluorofucose-treated or untreated labeled LS174T cells (500000 cells/well) and the plate was kept at 4° C. for 2 hr. Plates were read at 480 nm excitation and 520 nm emission (total cell reading) and then washed with DPBS four times, followed by fluorescent analysis. (see FIG. 4; The numeral 1 refers to 2-fluorofucose). Cells treated with 2-fluorofucose demonstrated diminished adhesion to selectins.

Example 3: 2-Fluorofucose Inhibits P-Selectin or E-Selectin Binding of Neutrophils Female Balb/c mice were given oral 2-fluorofucose in their drinking water (10 mM, 100 mM, n=3/group) or left untreated. Mice remained on the 2-fluorofucose-containing water through day 21 when blood was collected. Pre-dose bleeds were collected for baseline comparison. Total white cells/µL blood were determined by hemacytometer using Turk's solution (0.01% gentian violet in 3% acetic acid) to exclude red blood cells. RBCs were eliminated from the remainder of the blood by osmotic lysis for flow cytometric analysis. Cells were incubated with anti-Gr-1-FITC antibodies (BD Biosciences) to identify neutrophils, and a recombinant P-selectin-human Fc fusion protein (R&D Systems) or a recombinant E-selectin-human Fc fusion protein. Cells were washed and then incubated with a PE-labeled goat anti-human IgG-Fc secondary antibody (Jackson Immunoresearch) to detect bound P-selectin or E-selectin. Samples were collected on a FACSCalibur flow cytometer and analyzed using CellQuest software. The percentage of Gr-1+ cells was determined and absolute number of neutrophils was calculated using the total white cell number from the hemacytometer count. In addition, flow samples were gated for Gr-1+ cells to assess P-selectin or E-selectin binding to neutrophils by histogram analysis. The geometric mean of the P-selectin or E-selectin fluorescent signal was determined from the histogram. (See FIG. 5; The numeral 1 refers to 2-fluorofucose). At doses of 10 or 100 mM of 2-fluorofucose, blood neutrophil counts were significantly increased with concomitant loss in P-selectin and E-selectin binding.

Example 4: Fucose Inhibitor Suppresses Liver Inflammatory Marker in Sickle Cell Murine Model NY1DD sickle cell mice were given plain water or 20 or 100 mM 2-fluorofucose in their drinking water ad libitum for 7 days. The treatment and control group had four mice per treatment group. On day 7, the mice were sacrificed with $CO_2$. An EDTA blood sample was collected from the heart and the liver was removed and frozen in liquid nitrogen. Total white blood cell counts and differentials were performed by manual counting using a hemocytometer and Wright-stained blood smears, respectively. Nuclear extracts were prepared from nuclei isolated from liver homogenates. Western blots of the nuclear extracts were immunostained with antibodies to NF-κB phospho-p65 a marker of NF-κB activation.

Results: White blood cells counts were 16.3+3.2 (K/μL, mean+SD) in SCD mice treated with water. The white counts increased to 22.1+5.2 in SCD mice treated with 20 mM 2-fluorofucose and 34.2+7.2 in SCD mice treated with 100 mM 2-fluorofucose, respectively (p<0.05 for all pairwise comparisons). NF-κB in liver and other organs is activated in SCD mice compared to normal C57BL/6 mice. Nuclear NF-κB phospho-p65 was partially diminished in mice treated with 20 mM 2-fluorofucose and markedly decreased in mice treated with 100 mM 2-fluorofucose or heme (see FIG. 6)

Example 5: Fucose Inhibitor Prevents Venous Statis in Sickle Cell Murine Model

NY1DD sickle cell mice were given plain water or 20 or 100 mM 2-fluorofucose in their drinking water ad libitum for 7 days. On day 4, dorsal skin fold chambers were implanted onto the the mice (n=4). On day 7, flowing venules in the dorsal skin-fold chamber window were selected and mapped using intravital microscopy. Thereafter, the mice were infused via the tail vein with human stroma-free hemoglobin (0.32 μmols heme/kg), a known inducer of vascular stasis in SCD mice. At 1 and 4 hours after infusion the same venules were re-examined and the percentage of vessels that had become static (no flow) was recorded. A control group of NY1DD mice (n=3) with implanted dorsal skin-fold chambers was given water to drink and injected intraperitoneally with hemin (40 μmols/kg×3 days) a known inhibitor of vascular stasis.

Results: Infusion of hemoglobin induced 30% microvascular stasis at 1 and 4 hours in SCD mice treated with water (FIG. 2). Treatment with 20 mM 2-fluorofucose partially inhibited stasis at 1 and 4 hours (p<0.05 compared to water). Treatment with 100 mM 2-fluorofucose or heme inhibited stasis to 6.7% or less at 1 and 4 hours (p<0.025 compared to water). (FIGS. 7 and 8)

The present invention is not limited in scope by the specific embodiments described herein. Various modifications of the invention in addition to those described herein will become apparent to those skilled in the art from the foregoing description and accompanying figures. Such modifications are intended to fall within the scope of the appended claims. Unless otherwise apparent from the context any step, element, embodiment, feature or aspect of the invention can be used in combination with any other. All patent filings, and scientific publications, accession numbers and the like referred to in this application are hereby incorporated by reference in their entirety for all purposes to the same extent as if so individually denoted.

What is claimed is:

1. A method for treating sickle cell disease comprising administering to a subject having sickle cell disease an effective amount of a compound having the formula:

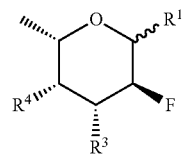

or a pharmaceutically acceptable salt or solvate form thereof, wherein the formula can be the alpha or beta anomer or the corresponding aldose form;
each of $R^1$, $R^3$, and $R^4$ is independently OH or a hydrolyzable ester group.

2. The method of claim 1, wherein said treatment reduces the incidence of vaso-occlusion in a subject having sickle cell disease or reduces the severity or duration of a vaso-occlusive event in a subject having sickle cell disease.

3. A method for reducing the incidence of vaso-occlusion in a subject having sickle cell disease or reducing the severity or duration of a vaso-occlusive event in a subject having sickle cell disease comprising administering to a subject having sickle cell disease an effective amount of a compound having the formula:

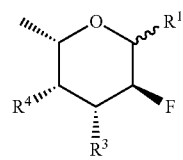

or a pharmaceutically acceptable salt or solvate form thereof, wherein the formula can be the alpha or beta anomer or the corresponding aldose form;
each of $R^1$, $R^3$, and $R^4$ is independently OH or a hydrolyzable ester group.

4. A method for treating sickle cell disease comprising administering to a subject having sickle cell disease an effective amount of 2-deoxy-2-fluorofucose to inhibit the binding of at least one of E-selectin or P-selectin to neutrophils.

5. The method of claim 1 wherein each of $R^1$, $R^3$, and $R^4$ is independently —OH or —OC(O)$C_1$-$C_{10}$ alkyl.

6. The method of claim 1 wherein each of $R^1$, $R^3$, and $R^4$ is independently —OH or —OC(O)$CH_3$.

7. The method of claim 1 wherein the compound is soluble in aqueous formulation buffer at a concentration of at least 1 mg/ml.

8. The method of claim 1 wherein the compound is soluble in aqueous formulation buffer at a concentration of at least about 100 mg/ml.

9. The method of claim 1 wherein the compound is soluble in aqueous formulation buffer at a concentration of at least about 300 mg/ml.

10. The method of claim 1 wherein following administration to a subject, the compound is converted in vivo to 2-deoxy-2-fluorofucose or a salt or solvate thereof.

11. The method claim 1, wherein treatment with the compound inhibits the binding of an adhesion molecule to leukocytes in the mammal by at least about 20%.

12. The method of claim 11, wherein said adhesion molecule is E-selectin, P-selectin, and/or L-selectin.

13. The method of claim 11, wherein said leukocytes are neutrophils.

14. The method of claim 1 wherein treatment with the compound inhibits leukocyte capture of red blood cells in the mammal by at least about 20%.

15. The method of claim 1 wherein treatment with the compound inhibits leukocyte rolling along on the endothelium in the mammal by at least about 20%.

16. The method of claim 1 wherein treatment with the compound inhibits leukocyte adhesion to the endothelium in the mammal by at least about 20%.

17. The method of claim 1 wherein treatment with the compound inhibits neutrophil extravasation in the mammal by at least about 20%.

18. The method of claim 1 wherein the compound is orally administered.

* * * * *